US011103277B2

(12) United States Patent
Arnold et al.

(10) Patent No.: US 11,103,277 B2
(45) Date of Patent: Aug. 31, 2021

(54) DEVICES AND METHODS FOR ATTACHING A MEDICAL DEVICE TO A SUBJECT

(71) Applicant: XACT ROBOTICS LTD., Caesarea (IL)

(72) Inventors: Ofer Arnold, Ma'ale Tzvia (IL); Yoav Tikochinsky, Tel-Aviv (IL)

(73) Assignee: XACT ROBOTICS LTD., Caesarea (IL)

(*) Notice: Subject to any disclaimer, the term of this patent is extended or adjusted under 35 U.S.C. 154(b) by 328 days.

(21) Appl. No.: 16/092,786

(22) PCT Filed: Apr. 7, 2017

(86) PCT No.: PCT/IL2017/050430
§ 371 (c)(1),
(2) Date: Oct. 11, 2018

(87) PCT Pub. No.: WO2017/179044
PCT Pub. Date: Oct. 19, 2017

(65) Prior Publication Data
US 2019/0125397 A1 May 2, 2019

Related U.S. Application Data

(60) Provisional application No. 62/390,944, filed on Apr. 15, 2016.

(51) Int. Cl.
A61B 17/34 (2006.01)
A61B 90/50 (2016.01)
(Continued)

(52) U.S. Cl.
CPC .......... A61B 17/3403 (2013.01); A61B 34/30 (2016.02); A61B 46/10 (2016.02);
(Continued)

(58) Field of Classification Search
CPC ...... A61B 17/3403; A61B 2017/00477; A61B 2017/00566; A61B 2017/00699;
(Continued)

(56) References Cited

U.S. PATENT DOCUMENTS 6,681,404 B1 1/2004 Adlard et al.
7,008,373 B2 3/2006 Stoianovici et al.
(Continued)

FOREIGN PATENT DOCUMENTS

CN 107095706 8/2017
JP 2001187066 A 7/2001
(Continued)

OTHER PUBLICATIONS

International Search Report of PCT/IL2017/050430 Completed Jul. 16, 2017; dated Jul. 16, 2017 2 pages.
(Continued)

Primary Examiner — Mohamed G Gabr
(74) Attorney, Agent, or Firm — The Roy Gross Law Firm, LLC; Roy Gross

(57) ABSTRACT

An apparatus for attaching a medical device to a subject's body, either directly to the subject's body or to an intermediary element on the subject's body. The apparatus prevents substantially any relative movement between the medical device and the subject's body. Such an apparatus comprises: (i) a back base positioned between the subject's body and a surface that the subject lies thereon, (ii) at least one set of straps connected to the back base and to at least one of the medical device and the intermediary element, and (iii) at least one set of connectors providing a connection between the at least one set of straps and one or more of the medical device, the intermediary element and the back base. The apparatus may further comprise any of pivoting connectors, a respiration sensor, and straps with a stretchable section. The apparatus may be used in combination with a sterile drape.

20 Claims, 17 Drawing Sheets

(51) Int. Cl.
*A61B 34/30* (2016.01)
*A61B 90/11* (2016.01)
*A61B 46/10* (2016.01)
*A61B 17/00* (2006.01)
*A61B 90/00* (2016.01)

(52) U.S. Cl.
CPC .............. *A61B 90/11* (2016.02); *A61B 90/50* (2016.02); *A61B 2017/00477* (2013.01); *A61B 2017/00566* (2013.01); *A61B 2017/00699* (2013.01); *A61B 2017/00876* (2013.01); *A61B 2017/3407* (2013.01); *A61B 2090/3983* (2016.02)

(58) Field of Classification Search
CPC .. A61B 2017/00876; A61B 2017/3407; A61B 2090/3983; A61B 34/30; A61B 46/10; A61B 90/11; A61B 90/50
See application file for complete search history.

(56) References Cited

U.S. PATENT DOCUMENTS

| | | | |
|---|---|---|---|
| 7,319,895 | B2 | 1/2008 | Klefstad-Sillonville et al. |
| 8,348,861 | B2 | 1/2013 | Glozman et al. |
| 2004/0133078 | A1 | 7/2004 | Edoga et al. |
| 2006/0229641 | A1 | 10/2006 | Gupta et al. |
| 2009/0112119 | A1 | 4/2009 | Kim |
| 2013/0281901 | A1 | 10/2013 | Ochoa |
| 2014/0155796 | A1* | 6/2014 | Yang ............... A61B 90/50 602/19 |
| 2014/0371584 | A1 | 12/2014 | Cleary et al. |
| 2015/0290017 | A1 | 10/2015 | Taylor et al. |
| 2016/0249990 | A1 | 9/2016 | Glozman et al. |
| 2018/0263597 | A1 | 9/2018 | Tchang et al. |

FOREIGN PATENT DOCUMENTS

| | | |
|---|---|---|
| JP | 2007502647 A | 2/2007 |
| JP | 2015165890 A | 9/2015 |
| WO | 200121084 A1 | 3/2001 |
| WO | 2011056217 | 5/2011 |
| WO | 2015052718 | 4/2015 |
| WO | 2015052719 | 4/2015 |
| WO | 2017115370 | 7/2017 |
| WO | 2017179044 A1 | 10/2017 |
| WO | 2019138277 | 7/2019 |

OTHER PUBLICATIONS

Written Opinion of PCT/IL2017/050430 Completed Jul. 16, 2017; dated Jul. 16, 2017.

* cited by examiner

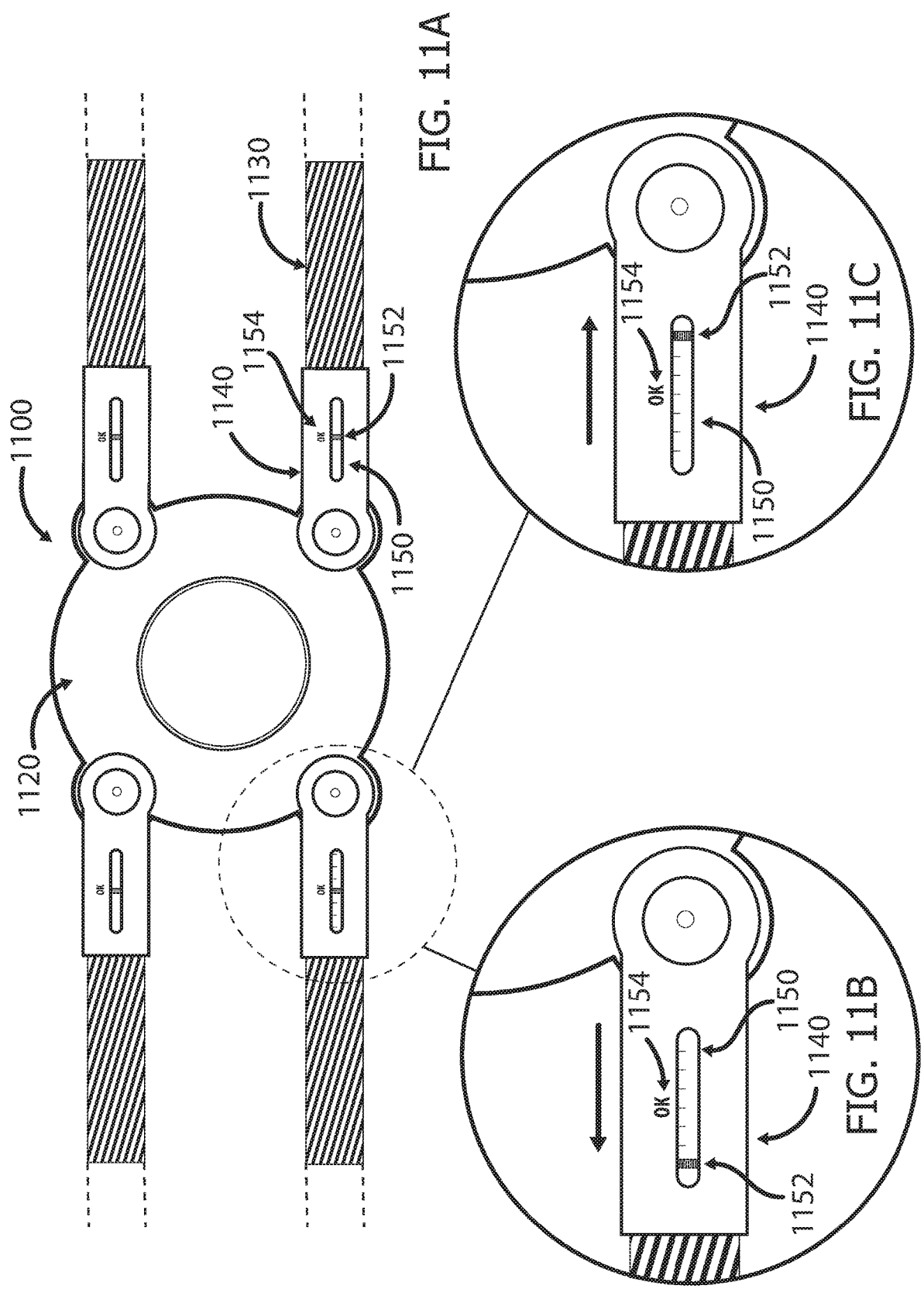

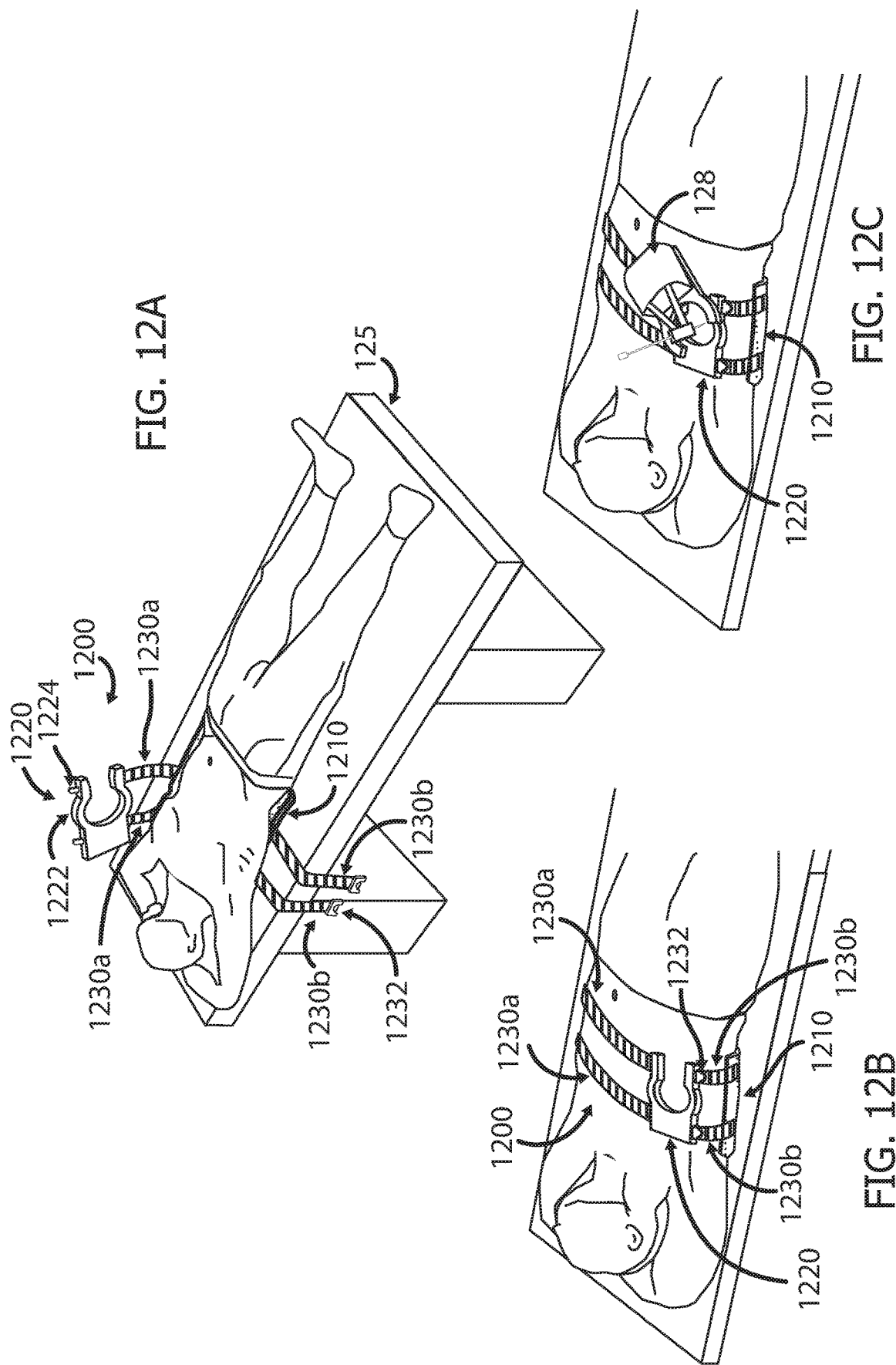

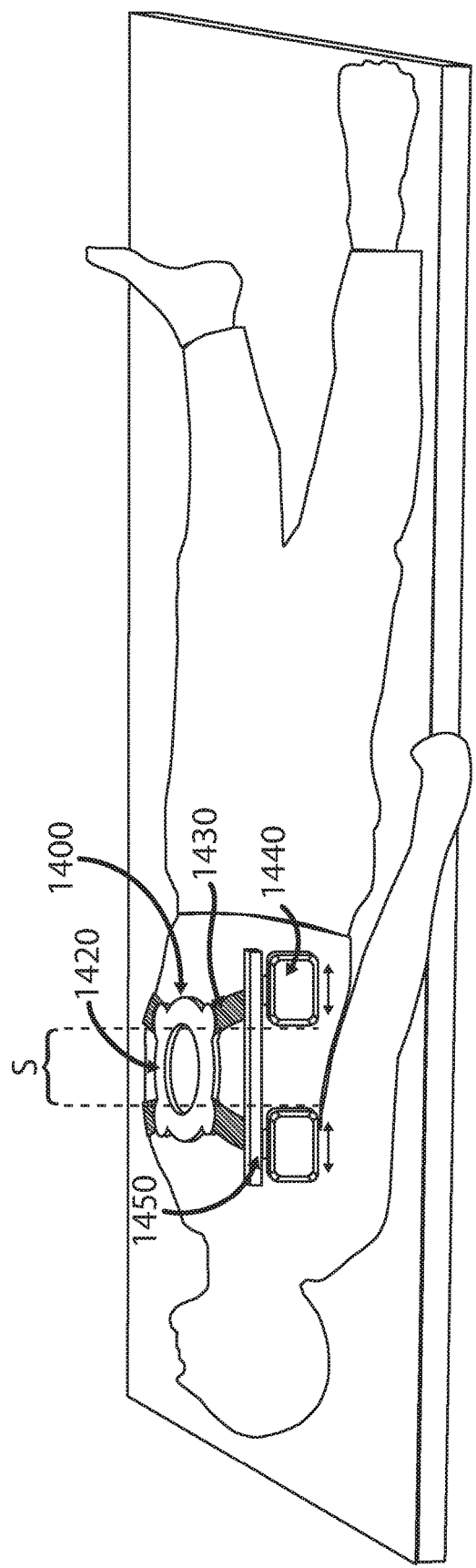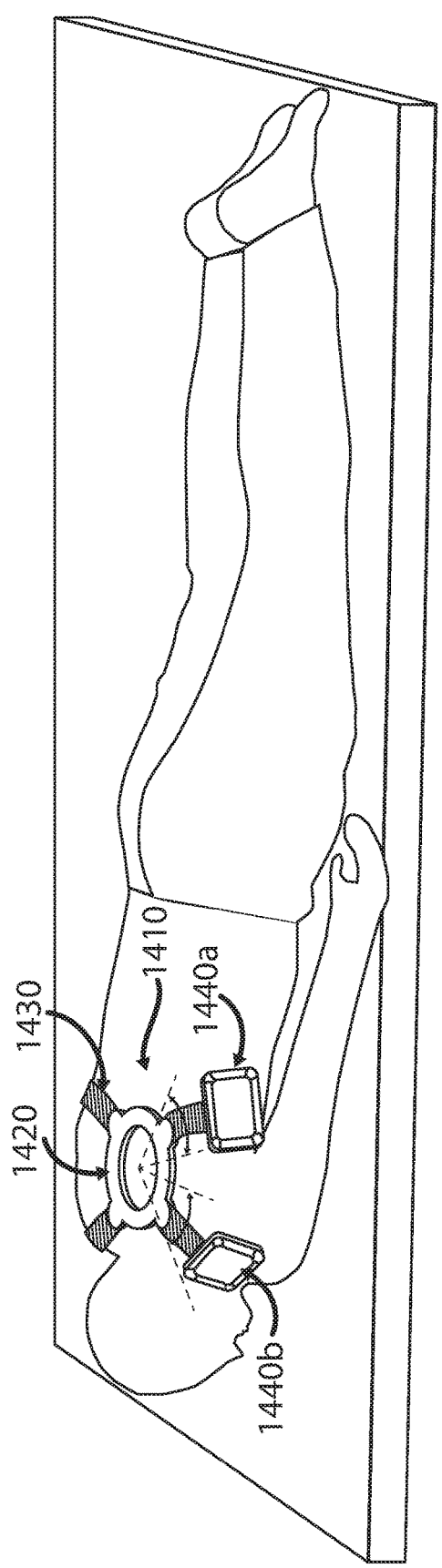

DEVICES AND METHODS FOR ATTACHING A MEDICAL DEVICE TO A SUBJECT

RELATED APPLICATIONS

This application is a National Phase of PCT Patent Application No. PCT/IL2017/050430 having International filing date of Apr. 7, 2017, which claims the benefit of priority of U.S. Provisional Application No. 62/390,944 filed on Apr. 15, 2016. The contents of the above applications are all incorporated by reference as if fully set forth herein in their entirety.

FIELD OF THE INVENTION

The present disclosure relates to the field of medical procedures, and specifically to devices and methods for attaching a medical device to a body of a subject.

BACKGROUND

Many routine treatments employed in modern clinical practice involve percutaneous insertion of medical tools, such as needles and catheters, for biopsy, drug delivery and other diagnostic and therapeutic procedures. The aim of an insertion procedure is to place the tip of an appropriate medical tool safely and accurately in a target region, which could be a lesion, tumor, organ or vessel. Examples of treatments requiring insertion of such medical tools include vaccinations, blood/fluid sampling, regional anesthesia, tissue biopsy, catheter insertion, cryogenic ablation, electrolytic ablation, brachytherapy, neurosurgery, deep brain stimulation and various minimally invasive surgeries.

Guidance and steering of needles in soft tissue is a complicated task that requires good three-dimensional coordination, knowledge of the patient anatomy and a high level of experience. Therefore, image-guided automated (e.g., robotic) systems have been proposed for performing these functions. Among such systems are those described in U.S. Pat. No. 7,008,373 to Stoianovici, for "System and method for robot targeting under fluoroscopy", and in U.S. Pat. No. 8,348,861 to Glozman et al, for "Controlled Steering of a Flexible Needle".

In recent years, body mounted automated devices and methods for planning their trajectories have been introduced. Some of these devices are guiding devices that help in choosing the insertion point and in aligning the needle with the insertion point and with the target and the physician then inserts the needle manually, and some are steering devices that also insert the needle towards the target, as disclosed, for example, in U.S. Application Publication No. 2006/0229641 to Gupta et al, for "Guidance and Insertion System", U.S. Application Publication No. 2009/0112119 to Kim, for "Rotating Biopsy Device and Biopsy Robot", U.S. Application Publication No. 2014/0371584 to Cleary et al, for "Patient Mounted MRI and CT Compatible Robot for Needle Guidance in Interventional Procedures" and U.S. Patent Application Publication No. 2016/0249990 to Glozman et al, for "Needle Steering by Shaft Manipulation".

Attaching the medical device to the patient's body is advantageous since it compensates for patient motion during the procedure as the device moves together with the patient. This minimizes tissue damage and patient discomfort which may be caused by relative movement between the device and the patient.

Gupta et al discloses a guidance and insertion device that is attached to the patient's body using tabs that tape the device's support base to the tissue surface or that include slots for receiving straps that secure the support base onto the patient Kim discloses a portable biopsy robot that is attached to the patient's skin using a strong adhesive located on the bottom of the robot. Cleary et al discloses a patient mountable robot that is attached to the patient's body using a four-adjustable-leg mechanism, each of the legs having an adhesive pad that directly contacts and sticks to the patient's body. Glozman et al discloses a robotic needle manipulator that is attached to the patient's body using belts or adhesives.

Direct attachment to the patient's skin using adhesives prevents a much-desired flexibility in positioning the automated device on the patient's body, and in re-positioning the device if necessary. Further, the use of adhesives does not allow placement of a sterile drape between the device and the patient's body in case the device is reusable and non-sterile, and may cause discomfort and skin irritation to the patient.

Thus, there is a need for devices and methods that overcome the deficiencies of the prior art.

The disclosures of each of the publications mentioned in this section and in other sections of the specification, are hereby incorporated by reference, each in its entirety.

SUMMARY

The present disclosure describes an apparatus for attaching a medical device (e.g., an insertion device) to the subject's body. The attachment apparatus may be configured to attach the medical device directly to the patient's body or it may comprise a mounting base configured to be placed on the patient's body and receive the medical device thereon. The medical device may be secured to the mounting base using securing elements, such as latches, magnets, etc.

In some implementations, the attachment apparatus may be positioned first on a medical surface, such as a patient bed, an imaging system (e.g., CT, MRI) bed, etc., and the patient then lies down on it. In other implementations, the attachment apparatus may be worn first by the patient who then lies down on the bed while wearing the attachment apparatus. In the latter case, the attachment apparatus may be configured as a vest, a harness, or any other suitable wearable unit.

The attachment apparatus may include a back base configured to be positioned between the patient's body and the patient bed and a plurality of straps.

In some implementations, the straps of the attachment apparatus may be rigidly connected to the back base such that their loose ends, either with or without connectors, e.g., buckles, are removably coupled to the medical device or to a mounting base. In alternative implementations, the straps may be rigidly connected to the mounting base or to the medical device such that their loose ends are removably coupled to the back base. In further implementations, the straps may be stand-alone components, initially unattached to either of the back base, the medical device or a mounting base, such that the user connects the straps to both the back base and the medical device or mounting base prior to the medical procedure. In even further implementations, both the back base and the mounting base or medical device may be provided with a plurality of straps connected thereto, and the user then secures the attachment apparatus to the patient by coupling the straps of the back base to the straps of the mounting base or medical device.

The straps, whether back base straps, mounting base/medical device straps and/or separate (initially unattached) straps, may be provided with connectors. The connectors may be snap buckles (female/male portions), hooks and loops fasteners (Velcro®), or any other suitable coupling mechanism.

The attachment apparatus may be adjustable, in order to fit a variety of different body types, shapes and sizes. The location on the patient's body where the medical device is to be placed in order to perform the medical procedure may also require adjustment of the attachment apparatus. In some implementations, the adjustment of the attachment apparatus may be via the back base, e.g., the back base may be adjustable in width and/or in length. For example, the back base may comprise two or more portions, which can be moved towards or away from each other, or the back base may comprise two or more portions which can slide along one another. In other implementations, the adjustment may be via the straps and/or the connectors. The straps may be elastic, at least in part, such that they can be stretched, or they may be substantially rigid but provided with a tightening mechanism, such as a tightening buckle through which the straps are threaded and then pulled for tightening.

In some implementations, the connectors connected to the back base, for example, and configured for mating with the strap connectors, may include a plurality of receiving members, so that the user can choose which receiving member to couple the strap connector to. Such receiving members may be niches connected by a channel along which the strap connectors can slide when not inserted into a niche, or they may be receiving portions of mechanical-magnetic snap fasteners.

The attachment apparatus may further include one or more cushions/pads to be placed underneath the medical device and/or the mounting base (if used) and/or the straps, to provide padding and minimize any discomfort or pain to the patient due to attachment of the medical device to his/her body. The cushion/s may also function as a booster/s to ensure stable positioning of the medical device, either directly or via a mounting base, on the curved surface of the patient's body. In some implementations, the cushion/s may be inflatable. In other implementations, the cushion/s may be filled, at least in part, with granules, either natural or artificial, such that when vacuum is applied to the cushion/s, the granules are pressed against each other and the cushion stiffens, providing stability to the medical device, and ensuring that there is substantially no relative movement between the medical device and the patient's body. The cushion/s may include therein (or thereon) one or more fiducial markers for determining the medical device's position during the procedure in case the medical device is positioned outside the scanned volume.

In some implementations, the connections between the straps and the medical device or mounting base may be such that at least one strap can pivot about an axis, providing a desired flexibility in the location and orientation of the medical device on the patient's body. For example, if the optimal positioning of the medical device in order to perform the medical procedure is on the upper chest of the patient, at least one strap may be rotated such that it is fastened over the patient's shoulder.

As the patient inhales, his/her lungs inflate, causing the chest/abdomen to expand radially. As the patient exhales, his/her lungs deflate, causing the chest/abdomen to shrink radially. In some implementations, the straps may include one or more stretchable sections, which can stretch during inhalation and return to their relaxed state during exhalation, thus ensuring that the straps do not become too tight during inhalation, which might cause the patient discomfort, and do not become too loose during inhalation, which might enable undesired movement of the medical device relative to the patient's body.

The straps or the strap connectors may further include indicators to indicate to the user if the connection of the straps is proper or improper, based on the tension value/degree.

In some implementations, the indicator may be the shape of a substantially rigid strap portion positioned adjacent the stretchable section of the strap, such that proper attachment of the strap may be if the substantially rigid strap portion is partially folded such that it can further straighten, during inhalation, and it can also further fold towards an "omega"-like (Ω) shape, during exhalation. In other implementations, the stretchable section of the strap may be coupled to a connector having an indication bar and a dial, which indicate to the user if the attachment of the straps is proper or improper by displaying the tension degree of the stretchable section, numerically or otherwise.

The attachment apparatus may further comprise a mounting base to which the medical device is coupled. The mounting base may include a base adapted to be placed on the patient's body, either directly or with a sterile drape therebetween, and one or more coupling members, such as latches or magnets, for mating with corresponding coupling members on the medical device, such as notches or magnetic material, respectively.

In some implementations, the mounting base may include a plurality of bases/plates which enable position adjustment and/or rotation of the medical device coupled thereto. Rotation of the medical device may be needed, for example, for orientating an insertion device according to an optimal needle insertion angle or for preventing imaging artifacts. In some implementations, the mounting base may include a stationary plate, a moveable plate coupled to the stationary plate and a rotating plate coupled to the moveable plate. The moveable plate may enable restricted movement in all directions and the rotating plate may enable pivoting about an axis. Once the desired positioning is achieved, the user ensures that the positioning is maintained by locking the plates of the mounting base such that they can no longer move/rotate. The rotating plate may alternatively be part of the medical device base such that is the user couple the rotating plate to the moveable plate upon coupling of the medical device to the mounting base.

In some implementations, the attachment apparatus may include a plurality of weights, which may be coupled to a mounting base or to a cushion/pad placed on the patient's body, such that the weights fall to opposite sides of the patient's body. The weights being pulled downwards by gravity maintains the position of the mounting base or cushion/pad, and thus the medical device coupled thereto, on the patient's body. The weights may be coupled to the mounting base or to the cushion/pad using straps. The coupling may be such that at least one strap can pivot about an axis, allowing the attached weight to hang over the patient's shoulder, thus providing a desired flexibility in the location and orientation of the medical device on the patient's body.

In some cases, if the medical device cannot be sterilized in its entirety, its non-sterile portions must be sufficiently covered by a sterile drape prior to commencement of the medical procedure. Thus, an attachment apparatus used in conjunction with a medical device which requires draping must be coupled to the medical device such that the sterile environment is not compromised.

In some implementations, the medical device may include anchors for securing the straps of the attachment apparatus thereto. The strap connectors may include hooks adapted to latch on to the anchors. The straps may be coupled directly to the hooks or they may be coupled to rotating members which are coupled to the hooks, such that they allow adjustment of the straps' location via pivoting of the straps after the hooks have been coupled to the anchors. The hooks may be adapted to latch on to the anchors over the drape. Alternatively, the hooks may be passed through an opening in the drape which is re-sealed around the hooks, using welding, gluing, or any other suitable means. Further, in some implementations, the hooks may be attached to the internal surface of the drape and the strap may be attached to the external surface of the drape.

There is thus provided in accordance with an exemplary implementation of the devices described in this disclosure, an apparatus for attaching a medical device to a body of a subject, the apparatus comprising:
(i) a back base configured to be positioned between the body of the subject and a surface adapted for the subject to lie thereon,
(ii) at least one set of straps configured to be connected to the back base and to at least one of the medical device and an intermediary element adapted for positioning on the body of the subject and for receiving the medical device thereon, and
(iii) at least one set of connectors configured to provide a connection between the at least one set of straps and one or more of the medical device, the intermediary element and the back base,
wherein the apparatus is configured to prevent substantially any relative movement between the medical device and the body of the subject upon attachment of the medical device to the body of the subject.

In such a described apparatus, the at least one set of connectors may comprise a first set of connectors configured to provide a connection between the at least one set of straps and the back base, and a second set of connectors configured to provide a connection between the at least one set of straps and the at least one of the medical device and the intermediary element.

In either of these implementations, the at least one set of straps may comprise a first set of straps configured to be connected to the back base, and a second set of straps configured to be connected to at least one of the medical device and the intermediary element. In such a case, one or more straps of the first set of straps may be configured to be connected to one or more straps of the second set of straps. In any of these apparatuses, one or more connectors of the at least one set of connectors may be configured to enable pivoting of at least a portion of the one or more connectors about an axis. In the latter case, the one or more connectors may comprise at least two coupled portions, wherein one of the at least two coupled portions may be configured to be attached to the at least one of the medical device and the intermediary element and another of the at least two coupled portions may be configured to be attached to a strap of the at least one set of straps.

In any of these apparatuses, one or more straps of the at least one set of straps may comprise at least one stretchable section configured to stretch along a longitudinal axis of the one or more straps. In such cases, the apparatus may further comprise an indicator configured to indicate the extent of the stretching of the at least one stretchable section. This indicator may comprise an indication bar and at least one marking.

In any of these implementations, one or more connectors of the at least one set of connectors may comprise a hook configured to be coupled to an anchor of the at least one of the medical device and the intermediary element. Such a hook may be adapted to be coupled to the anchor over a drape covering the medical device. Such a hook and one or more straps of the at least one set of straps may be configured to be attached to a drape covering the medical device, on either side of the drape.

In any of these implementations, there may be a respiration sensor configured to sense a characteristic associated with the breathing of the subject.

Furthermore, in any of the above-described apparatuses, the back base may be configured to enable adjustment of at least one of the length and the width of the back base. Likewise, the back base in any of these implementations may comprise at least two portions moveable relative to each other.

Yet other implementations may comprise a fastening member configured to be connected to the back base, the fastening member comprising a plurality of receiving elements configured to receive one or more connectors of the at least one set of connectors. In such an apparatus, the receiving elements may comprise niches and the fastening member further may comprise an elongate groove connecting the niches to each other, and the one or more connectors may be adapted to be moved within the elongate groove. In an alternative apparatus, one of the plurality of receiving elements and the one or more connectors may comprise a magnetic material and the other of the plurality of receiving elements and the one or more connectors may comprise a magnet.

In still other exemplary implementations, the intermediary element may comprise a mounting base, and the mounting base may include one or more coupling members configured to couple the medical device thereto. Such a mounting base may be configured to enable movement of the medical device relative to at least a portion of the mounting base upon coupling the medical device to the mounting base. Such a mounting base may comprise a stationary plate and a moveable plate configured to be connected to the stationary plate, the moveable plate being moveable relative to the stationary plate. The mounting base may further comprise a rotatable plate configured to be connected to the moveable plate and configured to pivot about an axis of connection to the moveable plate.

In any of these implementations, the intermediary element may comprise at least one flexible pad. Such a flexible pad may comprise a granular material enclosed within a flexible covering, and may be further configured to transform from a moldable state to a more structurally stable state by means of application of vacuum to the at least one flexible pad. Any such flexible pad may include one or more markers positioned either on or inside the at least one flexible pad, the markers being detectable by an imaging system.

In any of the above-mentioned implementations, the apparatus may be adapted to be donned by the subject prior to the subject lying on the surface. Furthermore, in any of these implementations, the surface may be a bed of an imaging system.

There is further provided in accordance with another exemplary implementation of the devices described in this disclosure, an apparatus for attaching a medical device to a body of a subject, the apparatus comprising:
(i) a back base adapted to be positioned between the body of the subject and a surface adapted for the subject to lie thereon, (ii) one or more straps configured to be connected to the back base and to at least one of the medical device and an intermediary element adapted for positioning on the body of the subject and for receiving the medical device thereon,
(iii) one or more first connectors configured to connect a first end of the one or more straps to the at least one of the medical device and the intermediary element, and
(iv) one or more second connectors configured to connect a second end of the one or more straps to the back base.

In such an apparatus, one or more connectors of at least one of the one or more first connectors and the one or more second connectors may be configured to enable pivoting of at least a portion of the one or more connectors about an axis. Furthermore, in such an apparatus, at least one of the one or more first connectors may comprise a hook configured to be coupled to an anchor of the at least one of the medical device and the intermediary element.

In such an apparatus, at least one of the one or more straps may comprise at least one stretchable section configured to stretch along a longitudinal axis of the at least one of the one or more straps. Such an apparatus may further comprise an indicator configured to indicate the extent of the stretching of the at least one stretchable section. Such an apparatus may further comprise a respiration sensor configured to be coupled to one of the one or more straps, the respiration sensor being configured to sense a characteristic associated with the breathing of the subject.

There is even further provided in accordance with yet another exemplary implementation of the devices described in this disclosure, an apparatus for attaching a medical device to a body of a subject, the apparatus comprising:
(i) a back base adapted for positioning between the body of the subject and a surface adapted for the subject to lie thereon,
(ii) one or more straps configured to be attached to an external surface of a drape configured to cover the medical device, the one or more straps being further configured to be connected to the back base,
(iii) one or more device connectors configured to be attached to an internal surface of the drape and further configured to be coupled to at least one of the medical device and an intermediary element adapted for positioning on the body of the subject and for receiving the medical device thereon.

In this implementation, the apparatus may further comprise one or more base connectors configured to provide the connection between the one or more straps and the back base. In such an apparatus, at least one of the medical device and the intermediary element may include anchors and the device connectors may comprise hooks configured to be coupled to the anchors.

Furthermore, there is also provided in accordance with other exemplary implementations of the devices described in this disclosure, an apparatus for attaching a medical device to a body of a subject, the apparatus comprising:
(i) one or more straps configured to be connected to at least one of the medical device and an intermediary element adapted for positioning on the body of the subject and for receiving the medical device thereon,
(ii) one or more weights configured to be coupled to the one or more straps.

In such an apparatus, the one or more weights may be configured to be coupled to the one or more straps by means of a bar, and the one or more weights may be moveable along the bar.

According to additional exemplary implementations of the methods described in this disclosure, there is further proposed an alternative method of attaching a medical device to a body of a subject, the method comprising:
(i) providing an attachment apparatus, the apparatus comprising:
  (a) a back base configured to be positioned between the body of the subject and a surface adapted for the subject to lie thereon,
  (b) at least one set of straps configured to be connected to the back base and to at least one of the medical device and an intermediary element adapted for positioning on the body of the subject and for receiving the medical device thereon, and
  (c) at least one set of connectors configured to provide a connection between the at least one set of straps and one or more of the medical device, the intermediary element and the back base,
wherein the attachment apparatus may be configured to prevent any substantial relative movement between the medical device and the body of the subject upon attachment of the medical device to the body of the subject,
(ii) positioning the back base of the attachment apparatus on the surface,
(iii) upon the subject lying down on the surface, positioning the at least one of the medical device and the intermediary element on the body of the subject,
(iv) if the intermediary element was positioned on the body of the subject, positioning the medical device on the intermediary element, and
(v) coupling the at least one of the medical device and the intermediary element to the back base of the attachment apparatus using the at least one set of straps and the at least one set of connectors.

In such an exemplary method, the at least one set of connectors may comprise a first set of connectors configured to provide a connection between the at least one set of straps and the back base and a second set of connectors configured to provide a connection between the at least one set of straps and the at least one of the medical device and the intermediary element.

Such one or more connectors of the at least one set of connectors may be configured to enable pivoting of at least a portion of the one or more connectors about an axis. Additionally, such one or more connectors of the at least one set of connectors may comprise a hook configured to be coupled to an anchor of the at least one of the medical device and the intermediary element. In such a method, the attachment apparatus may further comprise a respiration sensor configured to sense a characteristic associated with the breathing of the subject.

Yet other implementations described in this application perform a method of attaching a medical device to a body of a subject, the method comprising:
(i) providing an attachment apparatus, the apparatus comprising:
  (a) a back base configured to be positioned between the body of the subject and a surface adapted for the subject to lie thereon,
  (b) one or more straps configured to be connected to the back base and to at least one of the medical device and an intermediary element adapted for positioning on the body of the subject and for receiving the medical device thereon,
  (c) one or more first connectors configured to provide a connection between a first end of the one or more straps and the at least one of the medical device and the intermediary element, and (d) one or more second connectors configured to provide a connection between a second end of the one or more straps and the back base, (ii) positioning the back base of the attachment apparatus on the surface, (iii) upon the subject lying down on the surface, positioning the at least one of the medical device and the intermediary element on the body of the subject, (iv) if the intermediary element was positioned on the body of the subject, positioning the medical device on the intermediary element, (v) connecting the first end of the one or more straps to the at least one of the medical device and the intermediary element using the one or more first connectors, and (vi) connecting the second end of the one or more straps to the back base using the one or more second connectors.

There is finally provided in accordance with yet another exemplary implementation of the methods described in this disclosure, a method of attaching a medical device to a body of a subject, comprising:

(i) providing an attachment apparatus, the apparatus comprising:

(a) a first base configured to be positioned between the body of the subject and a surface adapted for the subject to lie thereon, (b) a second base configured to be positioned on the body of the subject and to receive the medical device thereon, (c) at least one set of straps configured to be connected to the first base and to the second base, and (d) at least one set of connectors configured to provide a connection between the at least one set of straps and one or more of the first base and the second base, (ii) positioning the first base on the surface, (iii) upon the subject lying down on the surface, positioning the second base on the body of the subject, (iv) securing the second base to the first base using the at least one set of straps and the at least one set of connectors, and (v) coupling the medical device to the second base.

Implementations of the devices and methods described above may further include any of the features described in the present disclosure, including any of the features described hereinabove in relation to other device or method implementation.

It is to be understood that although some examples used throughout this disclosure relate to attachment of insertion devices to the body of a subject, the disclosed attachment apparatus is not limited for use with insertion devices alone and may be used with any medical device that is intended for attachment to the subject's body. Further, it can be appreciated that "attachment" of the medical device to the subject's body is to be interpreted as meaning either direct attachment or attachment via an intermediary element, such as a mounting base and/or cushion, etc.

Also, it is to be understood that although some examples used throughout this disclosure relate to insertion of a needle into a subject's body, this is done for simplicity reasons alone, and the scope of this disclosure is not limited to attachment of devices for insertion of a needle alone to the patient's body, but may include attachment of devices for insertion of any tool intended to be inserted into a subject's body for diagnostic and/or therapeutic purposes, including a needle, port, introducer, catheter (e.g., ablation catheter), cannula, surgical tool, fluid delivery tool, or any other such insertable tool.

In addition, it is to be understood that the term "strap" used throughout this disclosure to describe means for securing a medical device to the patient's body, may include any element suitable to be wrapped around at least part of the patient's body, such as strings, wires, cables, etc.

Finally, the terms "user", "physician" and "clinician" are used interchangeably throughout this disclosure and they may refer to any person taking part in the performed medical procedure.

BRIEF DESCRIPTION OF THE DRAWINGS

Some exemplary implementations of the methods and systems of the present disclosure are described with reference to the accompanying drawings. In the drawings, like reference numbers indicate identical or substantially similar elements.

FIGS. 11A-11C show another implementation of straps having a flexible section to accommodate body movements associated with breathing, and an indicator for proper/improper attachment.

FIGS. 12A-12C show three steps of attaching a medical device to the patient's body using an attachment apparatus having a mounting base, according to exemplary implementations.

FIGS. 14A-14B show an exemplary attachment apparatus having a mounting base and a plurality of weights.

DETAILED DESCRIPTION

Figure 1:
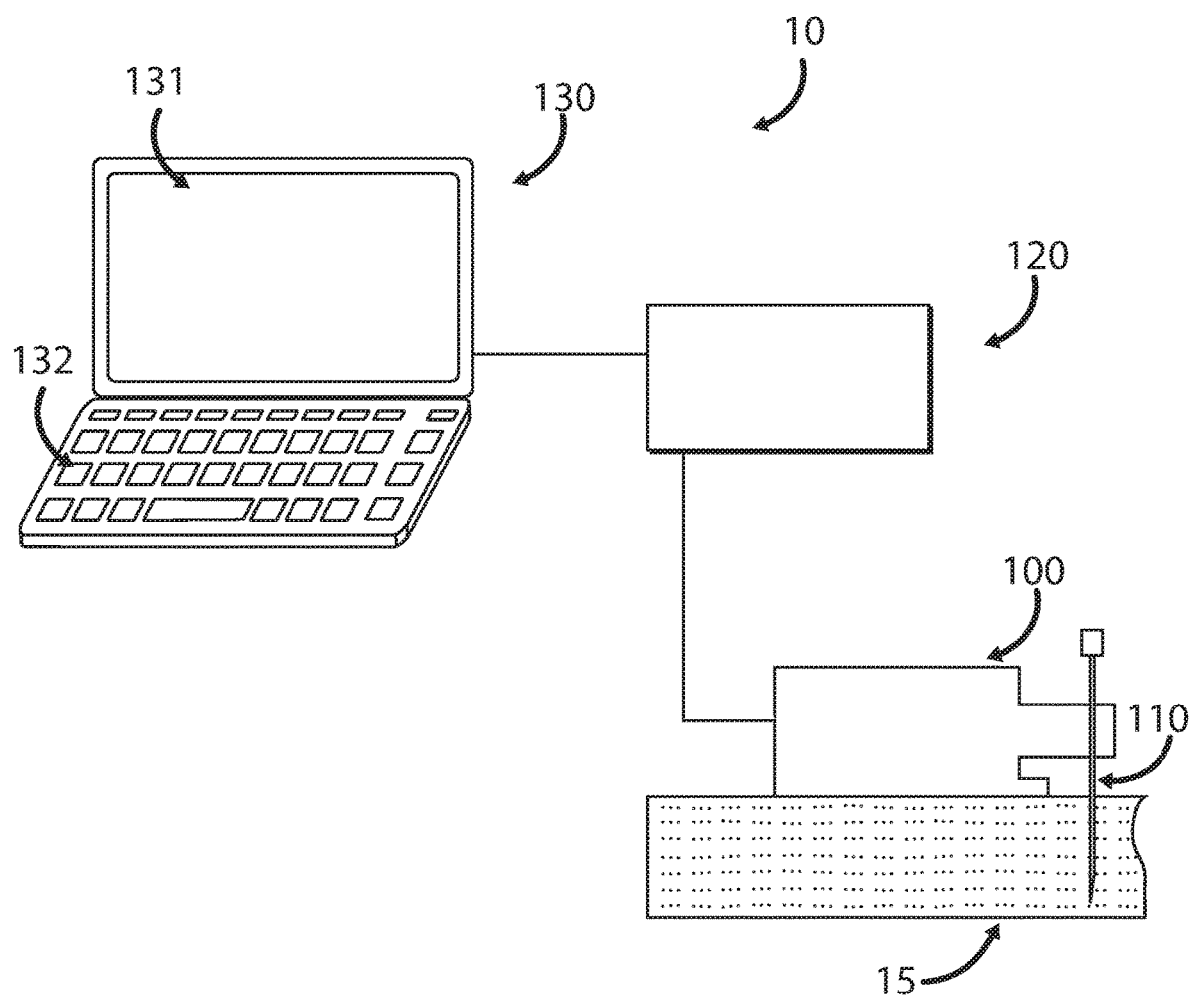
FIG. 1 shows a schematic diagram of an exemplary system for inserting a medical tool into the body of a subject.

FIG. 1 shows a schematic diagram of an exemplary medical system 10 which includes a body mountable device 100. In some implementations, the system 10 may be used for inserting a medical tool 110, e.g., needle, into the body of a subject 15. Such a system may include an automated insertion device 100 (e.g., robot), which may be additionally configured for steering the medical tool 110 during its insertion into the subject's body 15. The needle 110 may be removably coupled to the insertion device 100, such that the insertion device 100 can be used repeatedly with new needles.

In some implementations, the system 10 may include an imaging system, or it may be used in conjunction with an imaging system. The utilized imaging modality may be any one of X-ray fluoroscopy, CT, cone beam CT, CT fluoroscopy, MRI, ultrasound, or any other suitable imaging modality.

The system 10 may further comprise a computer 130, including at least one processor (not shown) and a display 131. The computer 130 may be a personal computer (PC), a laptop, a tablet, a smartphone or any other processor-based device. The computer 130 may also include a user interface 132, which may be in the form of buttons, switches, keys, keyboard, computer mouse, joystick, touch-sensitive screen, etc. The display 131 and user interface 132 may be two separate components, or they may form together a single component, such as a touch-sensitive screen ("touch screen").

The system 10 may further include a controller 120 (e.g., robot controller) for controlling the movement of the insertion device 100 and/or steering the needle 110 towards the target (e.g., lesion or tumor) within the subject's body 15. The controller 120 may be a separate component, as shown in FIG. 1. Alternatively, at least a portion of the controller 120 may be embedded within the insertion device 100, and/or within the computer 130.

Figure 2A:
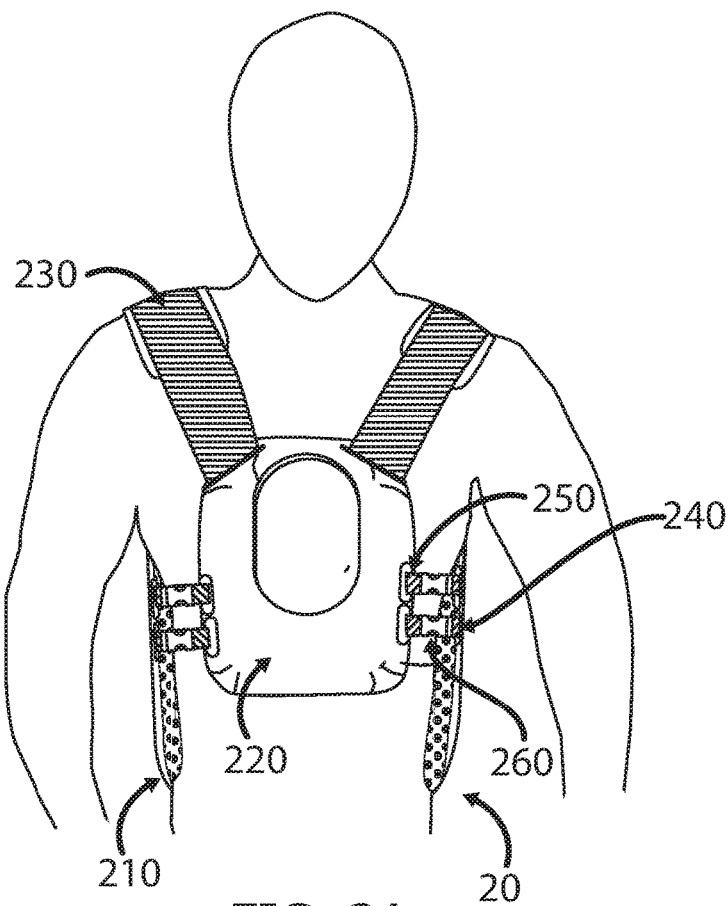
FIGS. 2A-2B show an exemplary wearable attachment apparatus for attaching a medical device to a body of a patient.

FIG. 2A shows a wearable attachment apparatus 20 to which a medical device, e.g. the automated insertion device 100 shown in FIG. 1, can be coupled. The wearable attachment apparatus 20 is intended to be worn by the patient before he/she lies down on the patient bed (21, shown in FIG. 2B). The wearable attachment apparatus may be configured, for example, as a vest, shirt, harness or any other suitable wearable garment. Once the patient lies down on the bed in the position suitable for his/her specific medical procedure, the medical device (28, shown in FIG. 2B), e.g., an insertion device, can be coupled to the attachment apparatus 20. The wearable attachment apparatus 20 may include a back base 210, a mounting base 220, to which the medical device is to be coupled, and straps attached to the back base 210 and/or to the mounting base 220. In some implementations, the attachment apparatus 20 may include two (or more) shoulder straps 230, connected to the back base 210 at their back ends and to the mounting base at their front ends ("back" and "front" referring to the location on the patient's body when the patient faces forward). The attachment apparatus 20 may further include a plurality of back base straps 240, which are connected to the back base 210 at one end and are initially unattached at the opposite end, and/or a plurality of mounting base straps 250 which are connected to the mounting base 220 at one end and are initially unattached at the opposite end. The back base straps 240 and the mounting base straps 250 may each include mating portions of a connector 260, such as female and male portions of a snap buckle, a hooks and loop fastener, etc., to couple the mounting base straps to the back base straps and thus connect the mounting base 220 to the back base 210. In some implementations, the attachment apparatus 20 does not include back base straps 240, and the mounting base straps 250 are coupled directly to the back base 210, using the connector/s 260. In some implementations, the attachment apparatus 20 does not include mounting base straps 250, and the back base straps 240 are coupled directly to the mounting base 220, using the connector/s 260.

In some implementations, the patient first dons the attachment apparatus 20 over his head such that the shoulder straps 230 are positioned properly on his/her shoulders, the back base 210 is placed against his back and the mounting base is placed against his/her chest and/or abdomen. The patient or the clinician then, using the buckles 260, couples the back base straps 240 to the mounting base straps 250, or the back base straps 240 directly to the mounting base 220, or the mounting base straps 250 directly to the back base 210, depending on the apparatus implementation, and tightens the back base straps 240 and/or the mounting base straps 250 to ensure that there is substantially no relative movement between the mounting base 220 and the patient's body. In some implementations, the back base 210 may be substantially rigid so as to provide support to the patient's body. In other implementations, the back base 210 may be substantially flexible so as to adjust more easily to the shape of the patient's body as the patient lies on the patient bed. Further, the back base 210 may be padded to enhance patient comfort.

Figure 2B:
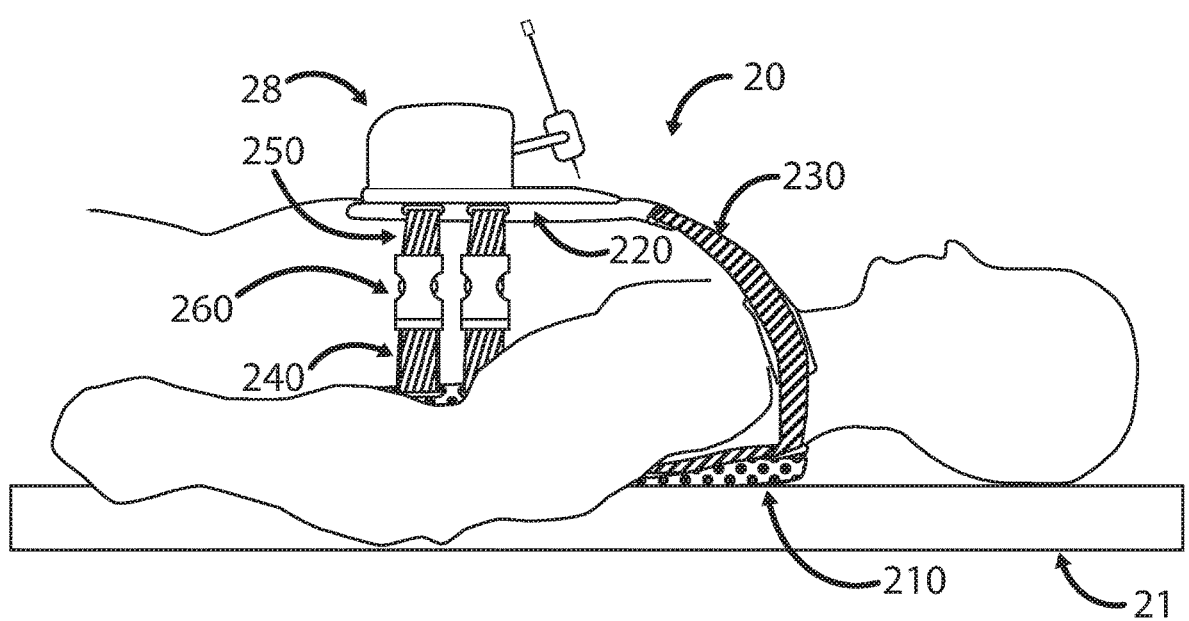

FIG. 2B shows the patient lying on the bed 21 while wearing the wearable attachment apparatus 20. Also shown is a medical device (e.g., an automated insertion device) 28 coupled to the mounting base 220. The coupling of the medical device 28 to the mounting base 220 may be established using connectors (not shown in FIG. 2B), such as latches, magnets, hooks and loops fasteners, adhesive, a combination thereof or any other suitable coupling mechanism.

Figure 3A:
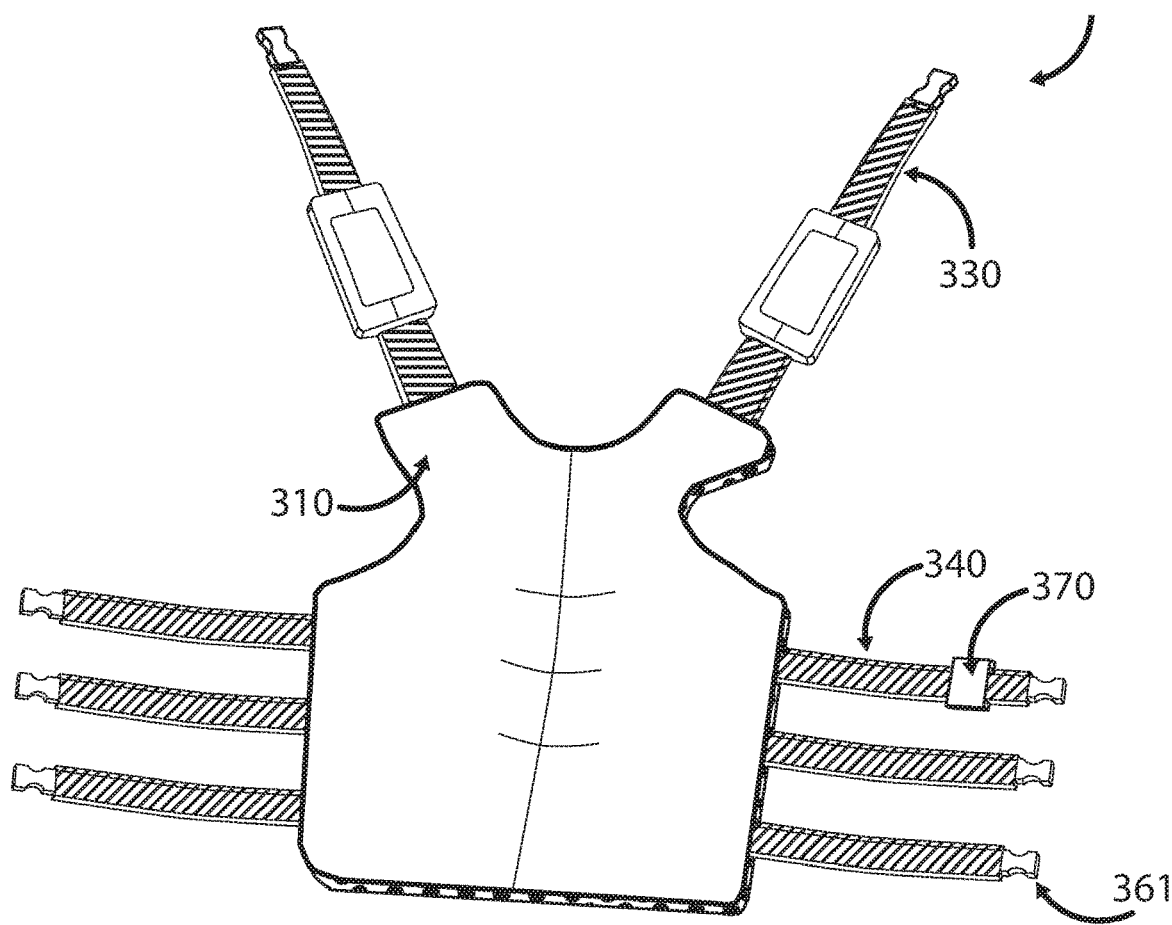
FIGS. 3A-3B show an exemplary attachment apparatus which is placed on the patient's bed and secured to the patient's body after the patient lies down on the bed.

FIG. 3A shows an exemplary attachment apparatus 30 which is placed on the patient bed first and secured to the patient's body only after he/she lies down on the bed. The attachment apparatus 30 may include a back base 310 and a plurality of straps attached to the back base 310. The straps may include shoulder straps 330 and side straps 340. In some implementations, the attachment apparatus 30 may include only side straps 340 or only shoulder straps 330. The free ends of the straps 330, 340, i.e., the ends not connected to the back base 310, may comprise a connector/fastener 361, or part thereof, such as a female or male end of a snap buckle, for connecting the straps 330, 340 to the medical device directly or via an intermediary element, such as a mounting base (not shown in FIG. 3A). In some implementations, after the back base 310 is placed on the patient bed, the patient lies down on top of it, and the attachment apparatus 30 is then secured to the patient by connecting the straps 330, 340 either to the medical device directly, such that the bottom surface of the device is positioned directly on the patient's body, or to an intermediary element such as a cushion or pad (not shown in FIG. 3A) or a dedicated mounting base, to which the medical device is coupled (not shown in FIG. 3A). In some implementations, whether the straps of the attachment apparatus 30 are connected to the medical device 38 directly, or to a mounting base, a cushion, or any other intermediary element, the coupling may be direct coupling, such as by means of a female/male portion of a buckle 362 located on the medical device 38 which mate with male/female portions of the buckle located at the free ends of the attachment apparatus' straps 330, 340, as shown, for example, in FIG. 3B. In case an intermediary element is used, the female/male portion of a buckle 362 may alternatively be located on the intermediary element (not shown).

In other implementations, the medical device 38, mounting base or cushion may be provided with additional straps having female/male portions of a snap buckle, for example, located at their free ends and configured to mate with male/female portions of the snap buckle located at the free ends of the attachment apparatus' straps 330, 340 (not shown in FIG. 3A).

The attachment apparatus 30 may further be provided with, or be adapted to have coupled thereto, a respiration sensor 370, which may be a pressure sensor or a sensor which senses the chest or abdominal expansion/contraction, and provides the physician with data regarding the breathing cycle of the subject, such as the respiration waveform. The respiration sensor 370 may be coupled to one of the straps 330, 340, either rigidly or removably, so that the user can choose which strap to couple the sensor to. The respiration sensor 370 may be provided with its own straps and connectors (e.g., female/male portions of a snap buckle), such that it can be removably connected to one of the straps 330, 340 at one end and to the medical device 38 or a mounting base, for example, at the opposite end. The connection may be direct or via connection to straps attached to the medical device or to the mounting base. In some implementations, the respiration sensor 370 may be coupled to a different component of the attachment apparatus, such as to the back base 310 or to the intermediary element, such as a pad/cushion placed under the medical device (as shown below in FIGS. 8A-8B). The data from the respiration sensor 370 may be transferred to the system controller (not shown in FIG. 3A) and may be used for synchronizing the activation of the medical device (e.g., the insertion and/or steering of a needle) and/or the initiation of a scan (e.g., a CT scan), with a specific point or points in the breathing cycle. The initiation of the scan may be automatic or the user may be prompted to manually initiate a scan. Respiration sensors which may be utilized are, for example, Respiration Sensor—SA9311M manufactured by Thought Technology Ltd. of Montreal West, Quebec, Canada, or the Piezoelectric Respiration (PZT) Sensor manufactured by Plux of Lisbon, Portugal.

It can be appreciated that a respiration sensor may also be utilized with the attachment apparatus implementation shown in FIGS. 2A-2B or with any other attachment apparatus implementation described hereinafter.

Figure 3B:
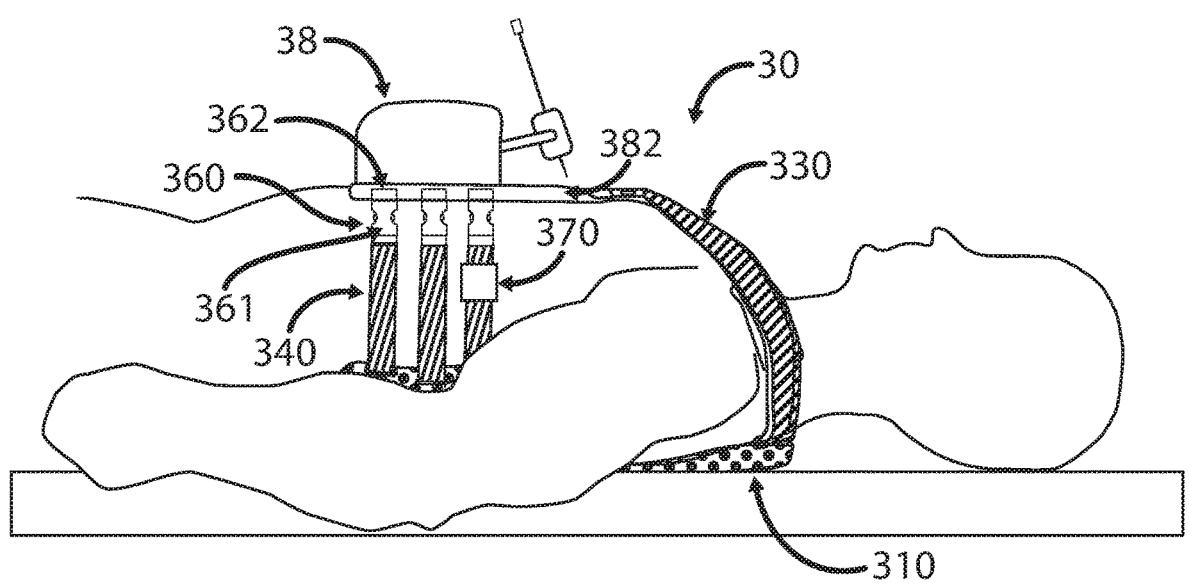

FIG. 3B shows the patient lying on the back base 310 of the attachment apparatus 30, with the medical device 38 placed directly on the patient's body and secured thereto by connection of the straps 330 and 340 of the attachment apparatus 30 directly to the base 382 of the medical device 38. In the implementation shown in FIGS. 3A and 3B, the connections are established via buckles 360 having female portions 361 attached to the attachment apparatus' straps 330 and 340 and male portions 362 attached to the medical device's base 382.

Figure 4A:
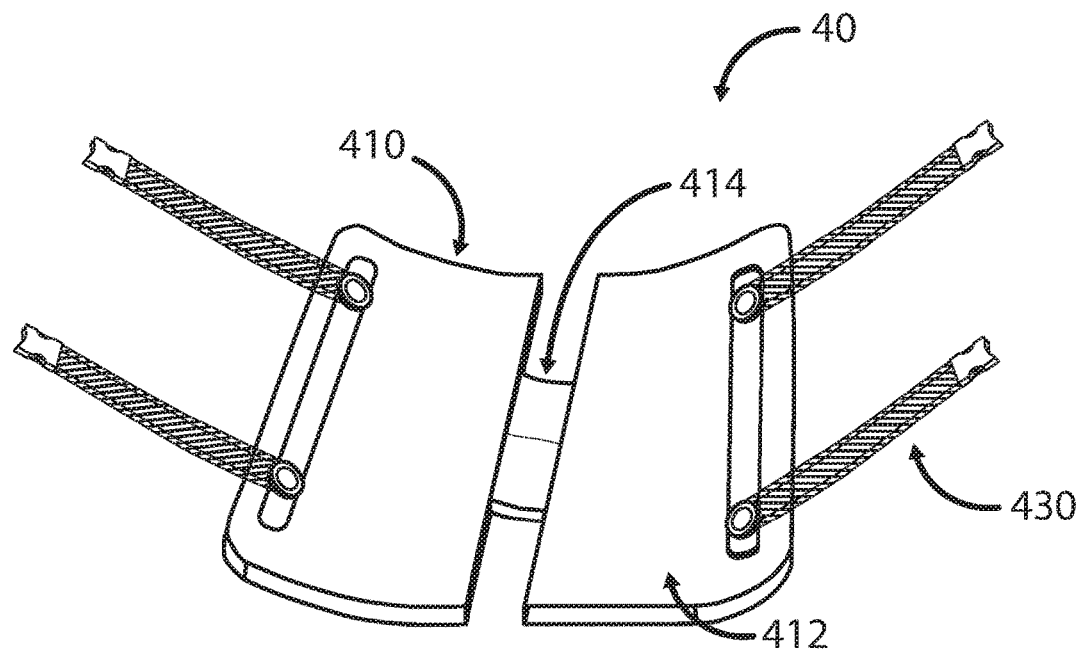
FIGS. 4A-4B show an exemplary adjustable attachment apparatus.
Figure 4B:
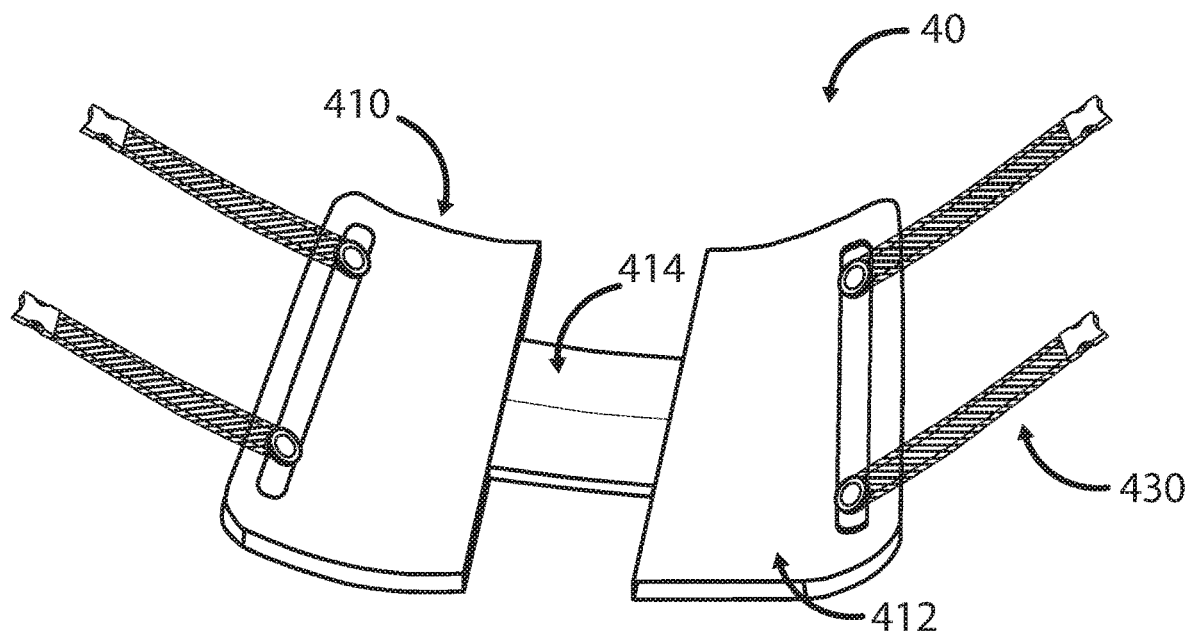

FIGS. 4A and 4B show an attachment apparatus 40 which can be adjusted to fit many different body sizes and shapes. The attachment apparatus 40 may have a back base 410 comprised of two or more portions 412 which can be moved towards each other, as shown in FIG. 4A, and away from each other, as shown in FIG. 4B. The two or more portions 412 may be identical or they may be different from each other. The back base portions 412 may be connected together by at least one connecting portion 414, which may be substantially perpendicular to the two back base portions 412. In some implementations, the connecting portion 414 may be substantially elastic, such that it can be stretched to move the two portions apart. In other implementations, the attachment apparatus 40 may include a mechanism, such as a sliding mechanism (not shown), that enables the two portions 412 to be moved along the connecting portion 414 and then fixated once the desired back base width (or length) is reached. Such a mechanism may be based on rails/grooves along the length of the connecting portion 414 and corresponding protrusions that can fit and move within the rails/grooves, a hooks and loops mechanism, etc. It can be appreciated that in addition to the back base 410 being adjustable, the length of the straps 430 may be adjustable to fit around the specific subject's body.

Figure 5:
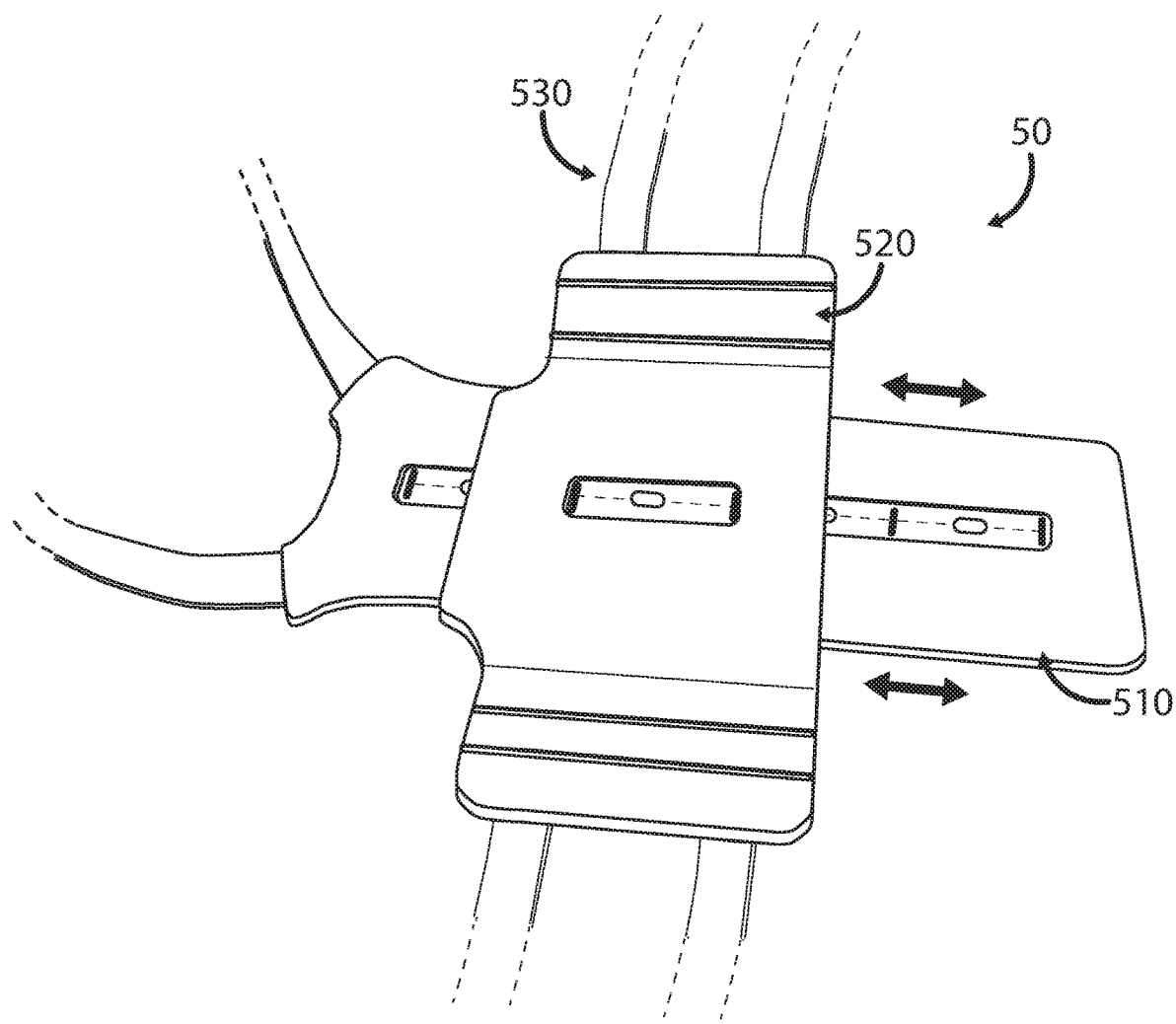
FIG. 5 shows another exemplary adjustable attachment apparatus.

FIG. 5 shows an attachment apparatus 50 in which the location of the back base straps 530 may be adjusted, according to the patient's body size and shape, the region of interest and/or the desired location for placing the medical device on the patient's body. The back base straps 530 may be coupled to the medical device and/or to a mounting base (not shown in FIG. 5). In some implementations, the attachment apparatus 50 may include a longitudinal part 510 ("longitudinal" being parallel to the length of the subject's body) and a lateral part 520, and at least one of the two parts can be moved along the other part. For example, the lateral part 520, or at least a portion of the lateral part 520, may be comprised of two layers (only the upper layer is shown in FIG. 5) connected to each other at opposite ends such that there is a space between them which can accommodate the vertical part 510.

In some implementations, after the longitudinal part 510 has been inserted through the double-layered portion of the lateral part 520, there is substantially unrestricted relative movement between the two parts. Thus, the attachment apparatus 50 can be used with patients of all shapes and sizes, and independent of the location on the patient's torso on which the medical device is to be positioned.

It can be appreciated, that alternatively, the longitudinal part 510 may be the double-layered part, at least in part, and the lateral part 520 may be the part which is inserted through the two layers of the longitudinal part 510. Further, it can be appreciated that any other mechanism which allows relative movement between the lateral part 520 and the longitudinal part 510 may be utilized.

FIGS. 6A-7B show two exemplary implementations of an attachment apparatus which allows the user to choose the location of the attachment apparatus' straps.

Figure 6A:
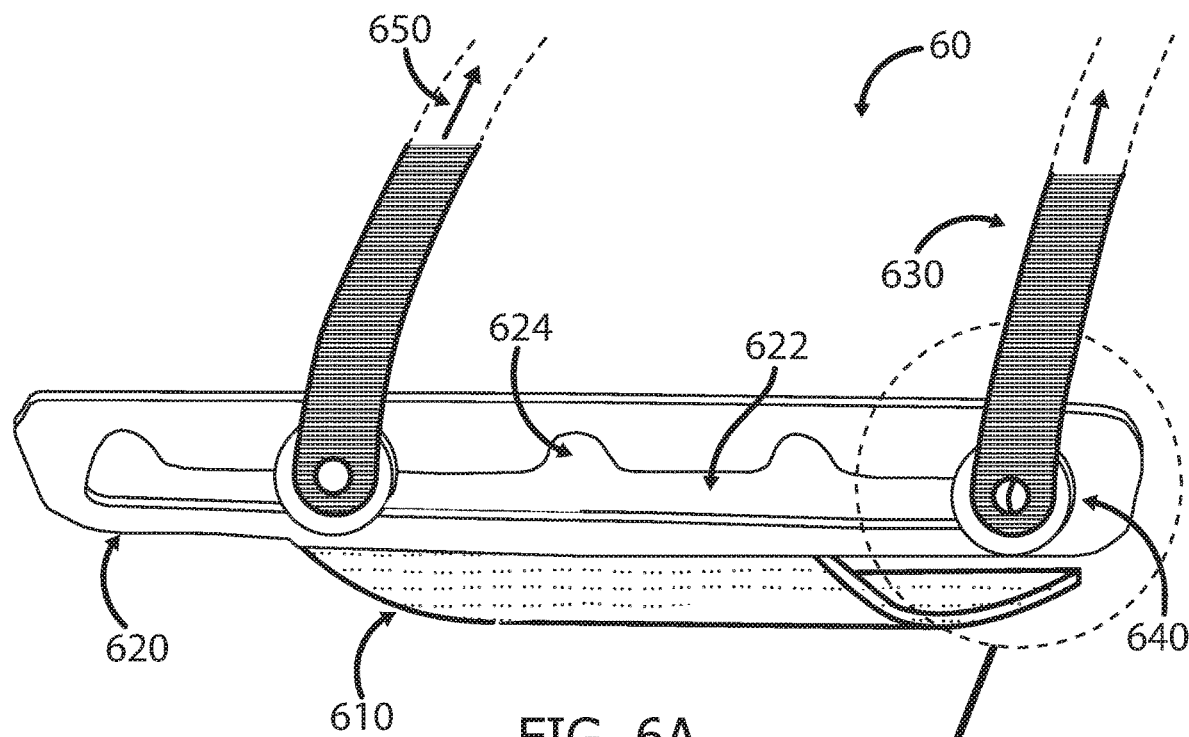
FIGS. 6A-6B show an exemplary attachment apparatus configured as a sliding fastener that enables the user to choose the positioning of the straps of the attachment apparatus.

FIG. 6A shows a partial view of an attachment apparatus 60 configured as a sliding fastener. The attachment apparatus 60 may include a back base 610 which may be flexible, at least in part, and an elongate buckle member 620 coupled to the back base 610. The buckle member 620 may include a channel (or groove) 622 and a plurality (e.g., five) of niches 624. The attachment apparatus 60 may further include at least one strap 630, which can be connected to at least one buckle member's niche 624. The strap 630 may include at its lower end, i.e., the end which is connectable to the buckle member's niches 624, a gripper 640 which can slide along the channel 622 of the buckle member 620 and be received within each of the niches 624, such that the user can choose which niche 624 to insert the gripper 640 into, based on the physical characteristics of the patient or on the patient's recumbent position, for example. The user then secures the attachment apparatus 60 to the patient by pulling the strap/s 630 in the direction of arrow 650, i.e., away from the back base 610, on which the patient is lying, and couples the strap/s 630 to the medical device or to a mounting base (not shown in FIG. 6A). Once the gripper 640 is received within a niche 624, and the strap 630 is pulled in the direction of arrow 650 and secured to the medical device or to the mounting base, the gripper 640 remains within the niche 624, thus preventing the gripper 640, with the attached strap 630, from sliding along the channel 622 of the buckle member 620.

Figure 6B:
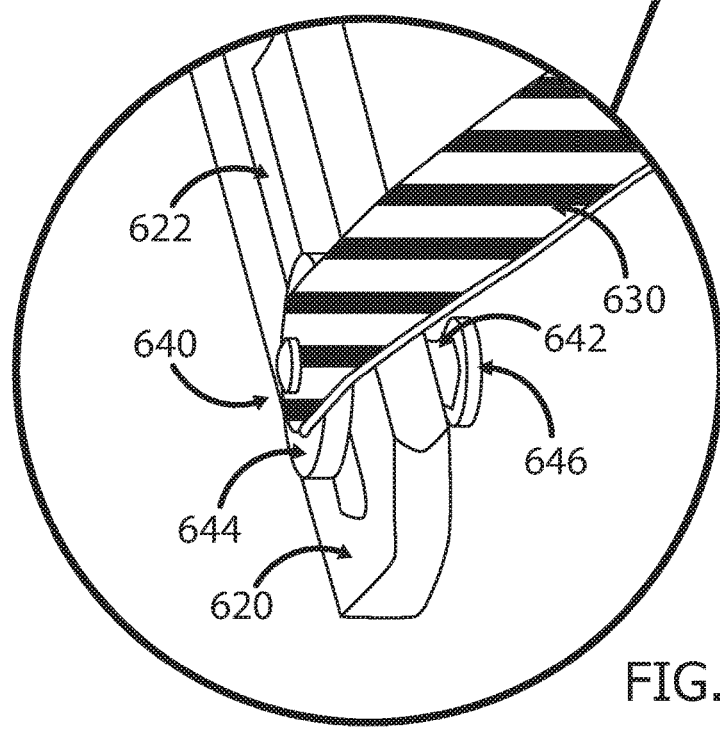

FIG. 6B shows a close-up view of the coupling between the strap 630 and the buckle member 620. The gripper 640 may include a short rod 642 with two constraining elements 644, 646 at its ends positioned on either side of the buckle member 620. The shape and size of the rod 642 should be such that the rod 642 can move freely along the channel 622 and into the niches 624. For example, if the rod 642 is configured as a tube, its diameter should be smaller than the width of the channel 622 which connects the niches 624, as well as smaller than the width/diameter of the niches 624. The shape and size of the constraining elements 644, 646 should be such that they prevent the gripper 640, and thus the strap 630, from disconnecting from the buckle member 620. For example, if the constraining members 644, 646 are configured as discs, their diameter/s should be larger than the width of the channel 622, and also larger than the width/diameter of the niches 624, so that each disc remains on its side of the buckle member 620 and cannot pass through the niches 624 and/or through the connecting channel 622. It can be appreciated that the two constraining elements 644, 646 may have different shapes and sizes.

Figure 7A:
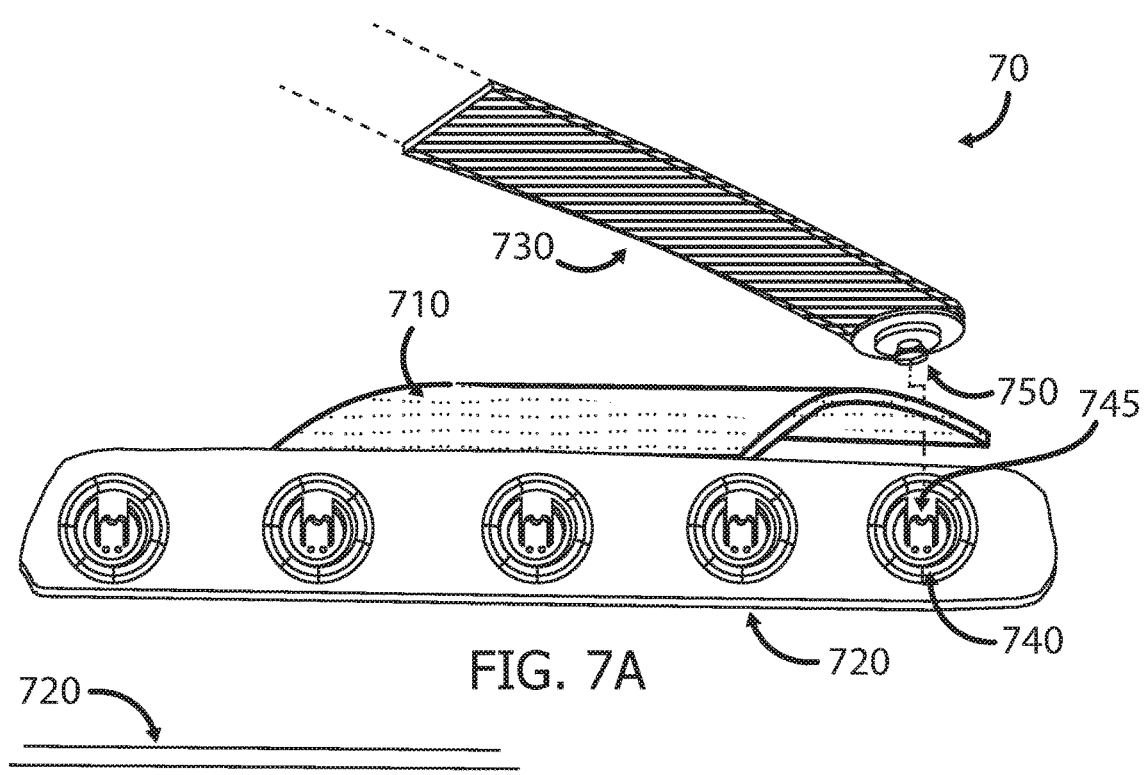
FIGS. 7A-7C show an exemplary attachment apparatus configured as a mechanical-magnetic snap fastener that enables the user to choose the positioning of the straps of the attachment apparatus.

FIG. 7A shows a partial view of an attachment apparatus 70 configured as a mechanical-magnetic snap fastener. The attachment apparatus 70 may include a back base 710 which may be flexible, at least in part, and a fastening member 720 attached to the back base 710 and having a plurality (e.g., five) of female connectors 740. The attachment apparatus 70 may further include at least one strap 730 having a corresponding male connector 750 (or vice versa, i.e., the fastening member may include male connectors and the straps may include female connectors). In some implementations, the male connector 750 may be manufactured, at least in part, from metal, and the female connector 740 may include magnetic material, or vice versa, such that positioning the male connector 750 in close proximity to the female connector 740 results in a magnetic connection between the two connectors. The female connector 740 may further include a release channel 745 for enabling disconnection of the male connector 750 from the female connector 740, by pulling the male connector 750 out through the release channel 745. In some implementations, the user can choose the optimal positioning of the strap/s 730 by choosing which female connector 740 to connect the male connector 750 to, and the attachment apparatus 70 can then be secured to the patient by pulling the strap/s 730 in the direction away from the back base 710, which is also the direction opposite the direction of the release channel 745, to ensure that the strap 730 does not unintentionally disconnect from the fastening member 720, and coupling the strap/s 730 to the medical device or to the/mounting base (not shown in FIG. 7A). A mechanical-magnetic snap fastener which may be utilized is the SNAP fastener manufactured by Fidlock GMBH of Hannover, Germany.

Figure 7B:
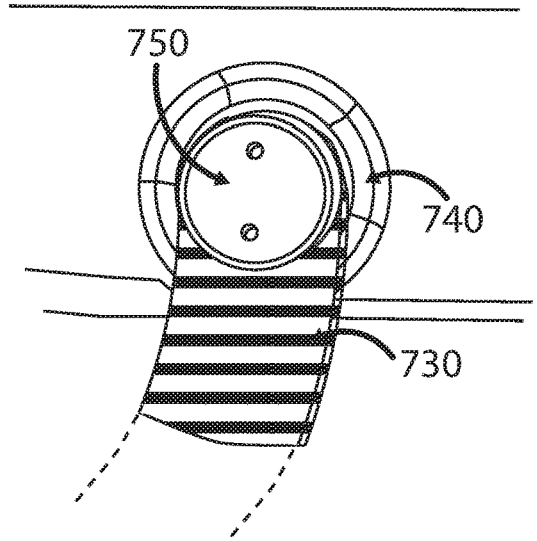

FIG. 7B shows a top view of the strap 730 connected to a fastening member 720 by means of a magnetic connection between the male connector 750 and the female connector 740.

Figure 7C:
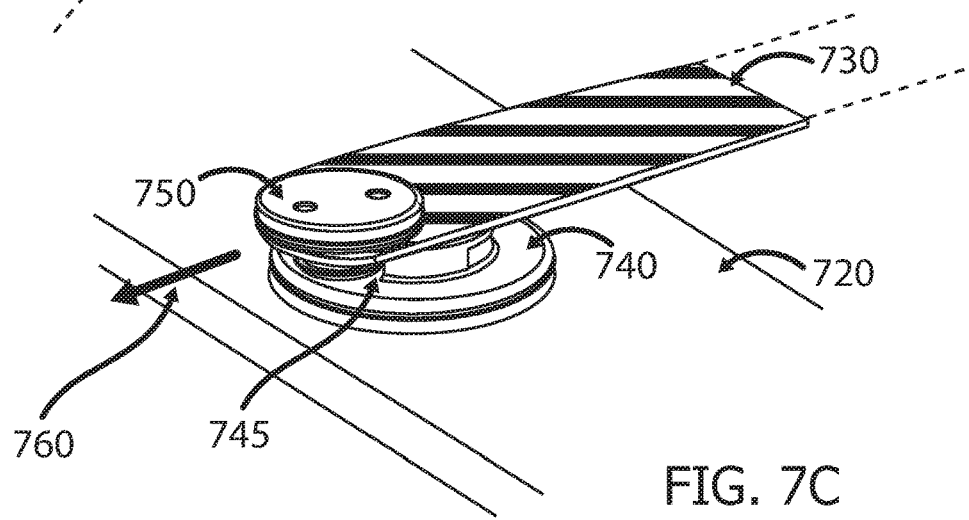

FIG. 7C shows a perspective view of the strap 730 being disconnected from the fastening member 720 by pushing (or pulling) the male connector 750 in the direction of arrow 760, thus releasing it from the grip of the female connector 740 along the release channel 745.

Figure 8A:
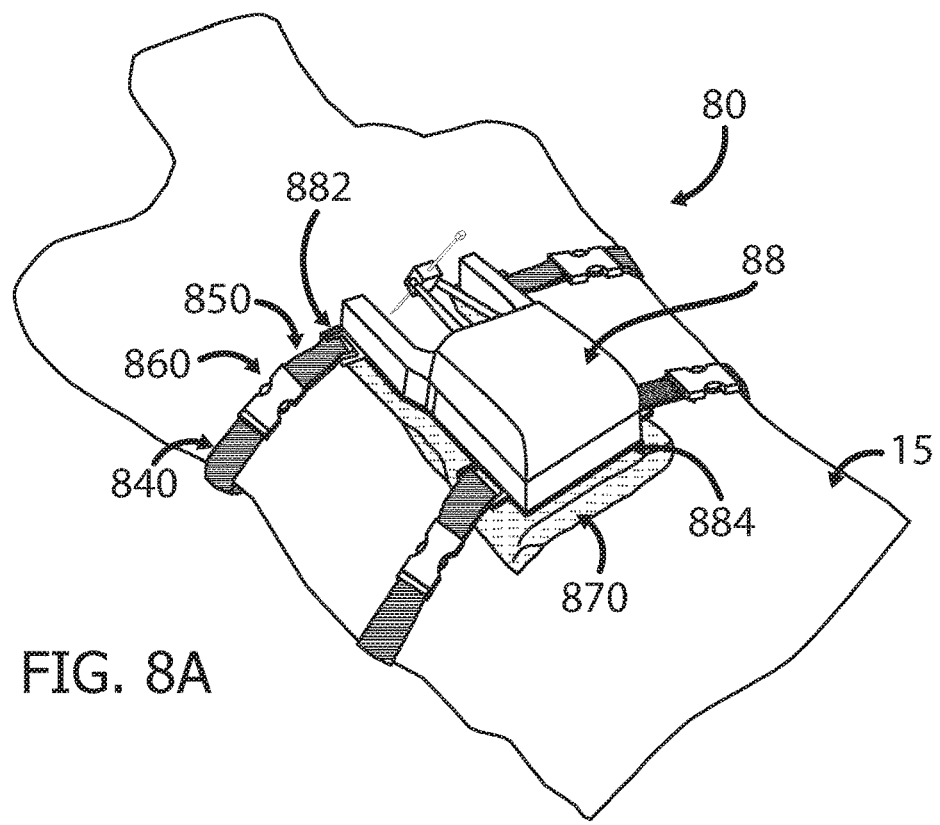
FIGS. 8A-8B show an exemplary attachment apparatus attached to a patient's body, with a medical device coupled thereto, and provided with a cushion.

FIG. 8A shows an attachment apparatus 80 which is connected directly to the medical device 88. The medical device 88 may include a plurality of anchors 882, to which straps are attached, either fixedly or removably. In some implementations, straps 850 of the medical device may be attached to the anchors 882 at one end and either directly to a back base (not shown in FIG. 8A) of the attachment apparatus or to straps 840 of the attachment apparatus, e.g., using buckles 860, at their opposite end. In other implementations, the attachment apparatus' straps 840 may be attached directly to the anchors 882 of the medical device 88. The anchors 882 may be attached to, or an integral part of, the device's base 884, or they may be attached to, or an integral part of, the device's housing. In some implementations, the anchors 882 may be configured as loops (circular, rectangular, etc.) through which the medical device's straps 850 or the attachment apparatus' straps 840 can be threaded. In other implementations, the anchors 882 may be provided with and/or configured as buckles or any other suitable fastening mechanism, to which the straps 840 or 850 are connected.

In some implementations, the anchors 882 may be positioned such that the connection of the straps to the anchors 882 takes place higher than skin level, in order to produce larger perpendicular forces and thus provide a more durable and stable attachment of the medical device to the patient's body.

Figure 8B:
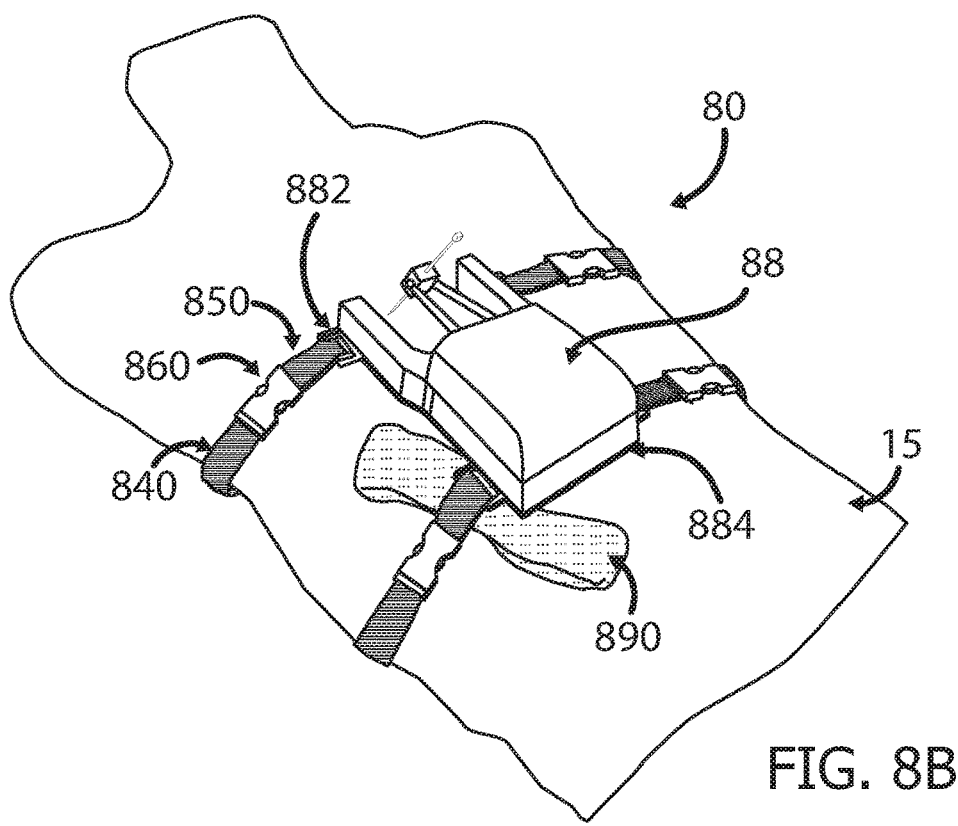

As discussed above in relation to FIG. 3A, in some implementations the medical device may be placed on or coupled to a dedicated intermediary element, such as a cushion (or pad), which is placed on the patient's body, as disclosed, for example, in the above referenced U.S. Patent Application Publication No. 2016/0249990. The size of the cushion may vary. In some implementations, the cushion may be a full-sized cushion 870 so that the entire base 884 of the medical device 88 can be placed on the cushion 870, as shown in FIG. 8A. In other implementations, the cushion may be a partial/local cushion 890, as shown in FIG. 8B. The cushion may be used to provide padding under the medical device 88 so as to minimize any discomfort or pain to the patient due to placement of the device directly on his/her body. Alternatively, or in addition, the cushion may have a functional role, such as being used as a booster for enabling stable positioning of the medical device 88 on a curved surface of the patient's body 15. In some implementations, several partial/local cushions may be used. The cushion 870, 890 may have anti-slip qualities due to its texture or by having a low adherence glue on its bottom surface, providing high friction forces between the medical device and the patient's skin and thus minimizing lateral movements of the device relative to the patient's skin. In some implementations, a sterile drape, such as Steri-Drape™ by 3M of Minnesota, U.S.A, may be placed on the patient's body around the treated area, and the cushion/s may be placed on top of the drape, i.e., between the medical device and the sterile drape. Further, in some implementations the medical device may be covered by an additional sterile drape, as shown below in FIGS. 15A-15C. In such implementations, the cushion/s may be placed between the drape sheet placed on the patient's body and the sterile drape covering the medical device. Alternatively, the cushion/s may be covered by the sterile drape together with the medical device.

In some implementations, the straps 840 or 850 may be coupled to the cushion and the medical device 88 may then be coupled to the cushion, e.g., by means of latches, magnets, a hooks and loops fastener, etc.

In some implementations, the cushion 870, 890 may be inflatable, such that its size and shape can be controlled and adjusted as needed. In some implementations, the cushion 870, 890 may be filled, at least in part, with granules (not shown), either natural or artificial, such as coffee beans, rice, sand, plastic beads, etc. In such implementations, the cushion may further include a vacuum valve (not shown), such that when vacuum is applied to the cushion 870, 890 via the valve, the granules are pressed against each other and the cushion stiffens. Further, the bottom portion of the cushion 870, 890 may conform to the shape and contour of the patient's body once placed on the patient's body, and the vacuum applied thereafter maintains the cushion's form throughout the medical procedure, thus providing further stability to the medical device 88 and minimizing discomfort to the patient. After vacuum is applied, the shape of the cushion 870, 890 cannot be altered until the vacuum is cancelled and air is allowed back into the cushion. In some implementations, at least a portion of the cushion 870, 890 may further include one or more fiducial markers, which form together an adjustable registration frame for determining the medical device's position at any point during the procedure in case it is outside the scanned volume, as described in co-owned International Patent Application No. PCT/IL2016/051396 to Roth et al, for "Adjustable Registration Frame", which is hereby incorporated by reference in its entirety.

Figure 9A:
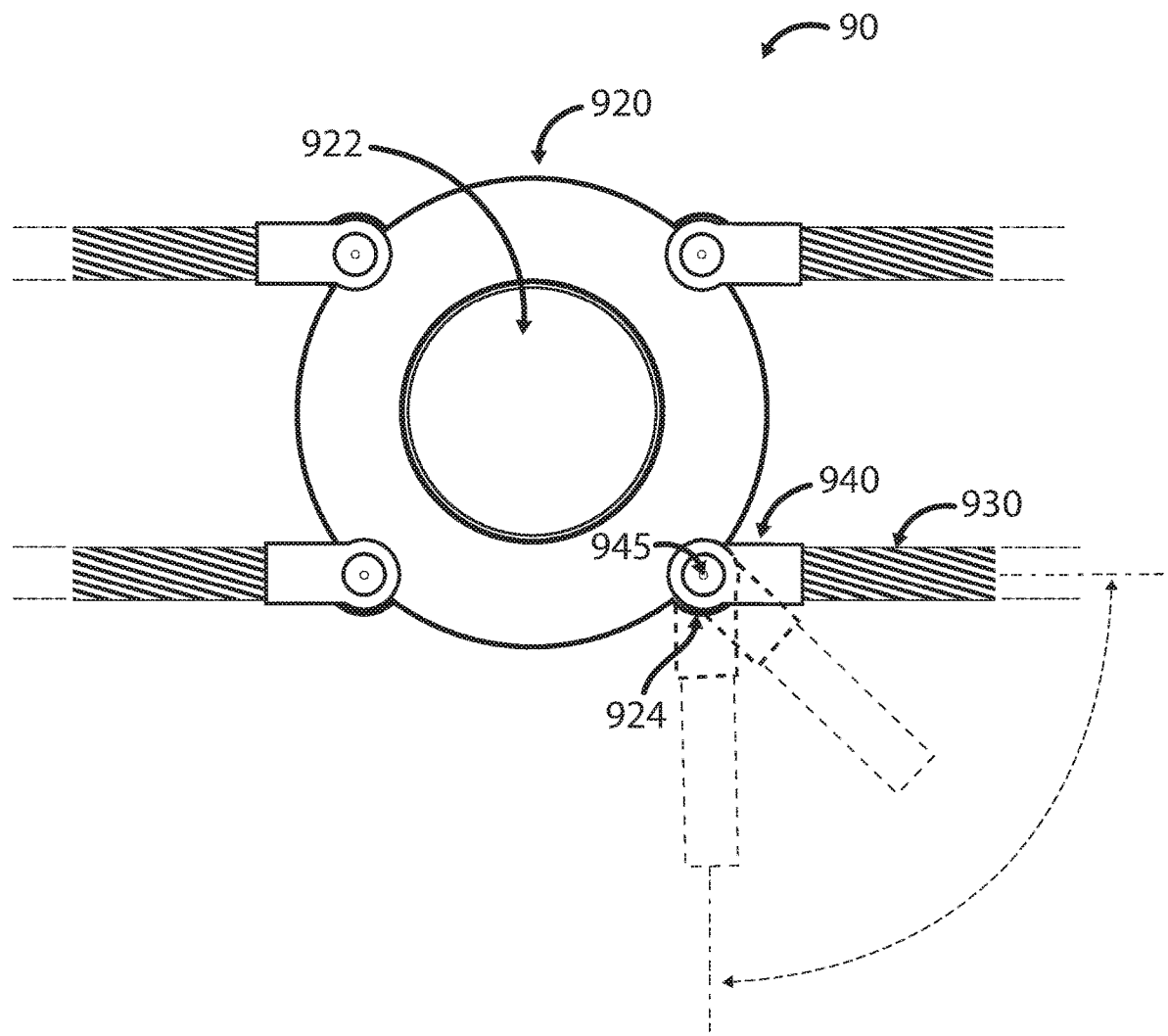
FIGS. 9A-9C show an exemplary attachment apparatus having a mounting base for receiving the medical device and straps which can pivot about an axis.

FIG. 9A shows an attachment apparatus 90 which includes a mounting base 920 for receiving the medical device thereon. The mounting base 920 may be circular, as shown in FIG. 9A, or it may be rectangular, triangular, a combination thereof or any other shape. The mounting base 920 may have an opening 922 to allow access of a medical tool (e.g., needle) of the medical device coupled to the mounting base 920 to the body of the patient, as shown in FIG. 9A, or it may be open-ended (e.g., having a "U" shape), as shown, for example, in FIGS. 12A-12C below. The mounting base 920 may further comprise at least a portion of a coupling mechanism (not shown) for receiving and securing the medical device thereto. For example, the mounting base 920 may include latches which mate with corresponding notches on the medical device base.

The mounting base 920 may be connected to a back base (not shown in FIG. 9A) of the attachment apparatus 90 using a plurality of straps 930. The straps 930 may be initially attached either to the mounting base 920 or to the back base. In case the straps 930 are provided together with the mounting base 920, they may be connected by the user either directly to the back base or to an additional set of straps (not shown in FIG. 9A), which are initially attached to the back base. In case the straps 930 are provided together with the back base, they may be connected by the user to the mounting base 920 only after the mounting base 920 is placed on the patient's body, and the connection may be either directly to the mounting base 920 or via an additional set of straps.

In some implementations, the connection between the straps 930 and the mounting base plate 920 is via strap connectors 940, which allow at least one strap to pivot about an axis, as shown in FIG. 9A. The mounting base 920 may include dedicated extensions 924 to which the strap connectors 940 are connected, for example using hinges 945, to enable the rotation of the straps 930. The ability to rotate the straps 930 provides a much-desired flexibility in the location and orientation of the mounting base 920, and thus the medical device, on the patient's body. It can be appreciated that such pivoting of the straps 930 may be similarly enabled in case the straps are connected directly to the medical device, as shown, for example, in FIGS. 14A and 14B below.

Figure 9B:
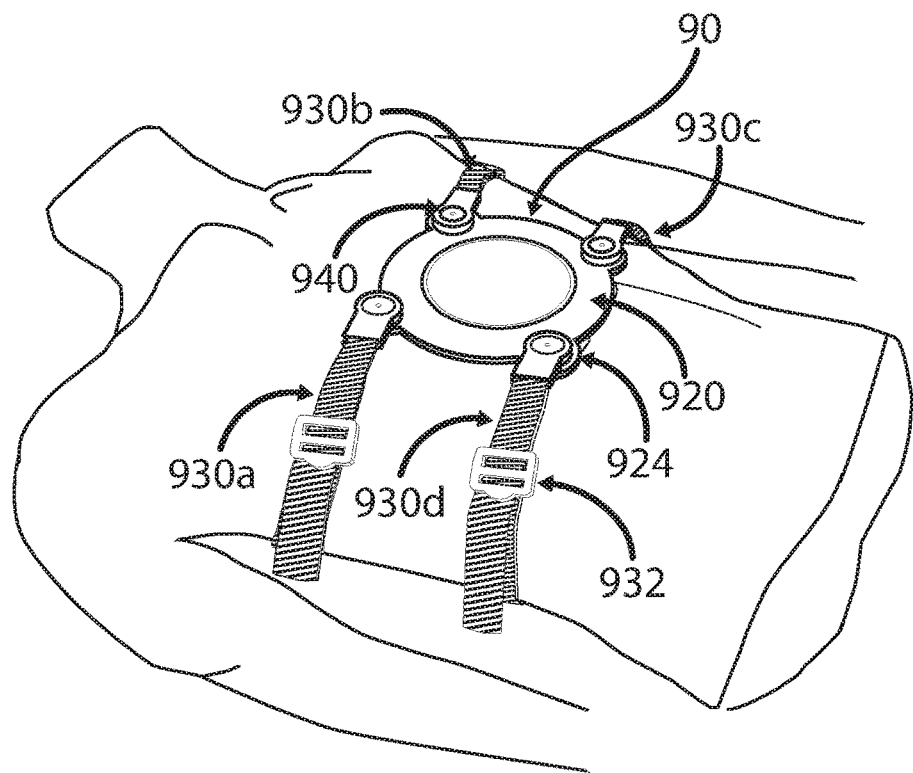
Figure 9C:
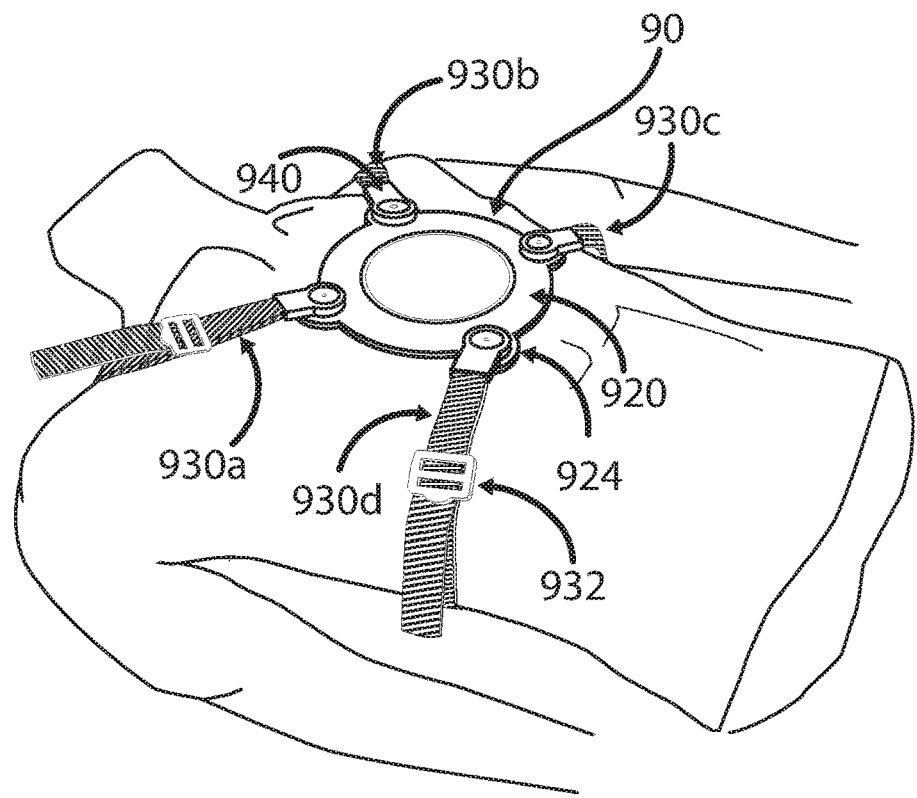

FIGS. 9B-9C show two exemplary options of attaching the attachment apparatus 90 of FIG. 9A to the patient's body. In FIG. 9B all the straps 930a-930d are used as side straps, i.e., they are all wrapped around the patient's torso, such that the upper straps 930a, 930b may be substantially parallel to the lower straps 930c, 930d ("upper" and "lower" refer to the position along the length of the patient's body, the head being the top and the feet being the bottom). The straps 930a-930d may further include a tightening mechanism, such as a tightening buckle 932 through which the straps 930a-930d are threaded and then pulled for tightening. It can be appreciated that such a tightening mechanism may be implemented in any one of the attachment apparatus implementations described throughout the present disclosure and it is not limited to the implementation shown in FIGS. 9B-9C.

In FIG. 9C the desired positioning of the attachment apparatus 90 is achieved by wrapping the two lower straps 930c, 930d around the patient's torso, whereas the two upper straps 930a, 930b are rotated and used as shoulders straps.

As the patient inhales, his/her lungs inflate, causing the chest/abdomen to expand radially. As the patient exhales, his/her lungs deflate, causing the chest/abdomen to shrink radially. Thus, if the straps which secure the medical device or the mounting base to the patient's body have no flexibility, there is a risk that they might become too tight during inhalation, which might cause significant discomfort to the patient, and/or that they become too loose during exhalation, which might enable relative movement between the medical device and the patient's body. Such relative movement might cause not only significant discomfort to the patient, but also physical harm to the patient, such as tearing of tissues due to uncontrolled sudden movements of the medical tool while it is positioned inside the patient's body. Further, in some insertion devices, steering of the medical tool is based on the assumption that there is no relative movement between the device and the patient's body, thus, relative movement between the device and the patient's body might impair the accuracy of the device and compromise the success of the medical procedure.

To eliminate the above risks, the straps which attach the medical device to the patient's body may include one or more elastic (or—flexible) sections, which can stretch during inhalation and return to their relaxed state during exhalation, thus ensuring that the straps do not become too tight during inhalation so as to cause the patient discomfort, and do not become too loose during inhalation so as to enable undesired movement of the medical device relative to the patient's body.

Figure 10A:
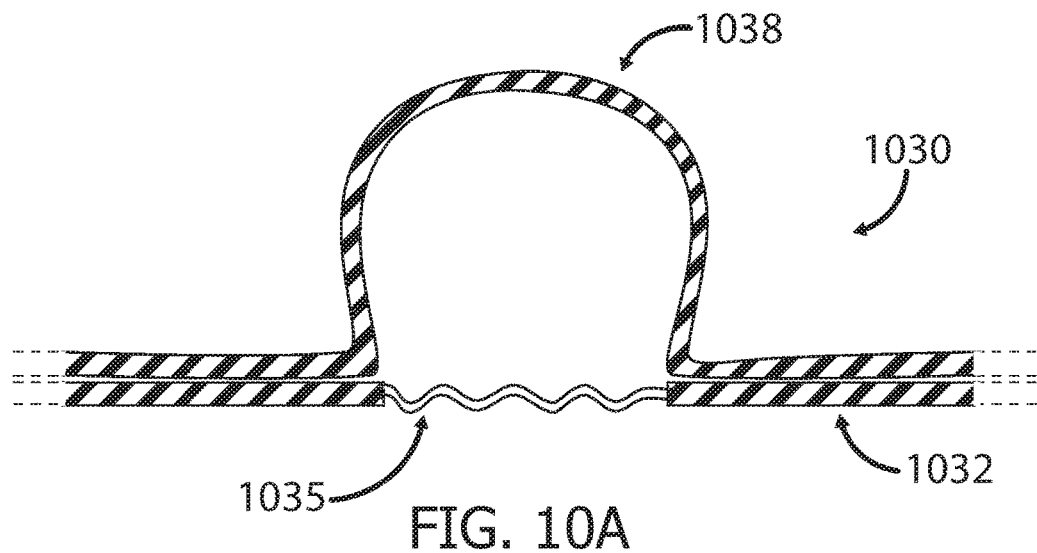
FIGS. 10A-10C show partial cross-sectional views of exemplary straps having a flexible section to accommodate body movements associated with breathing.
Figure 10B:
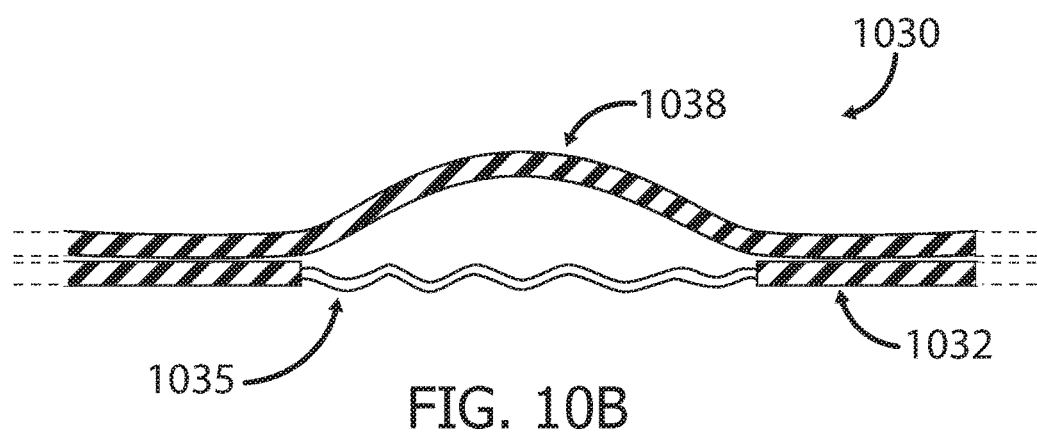
Figure 10C:
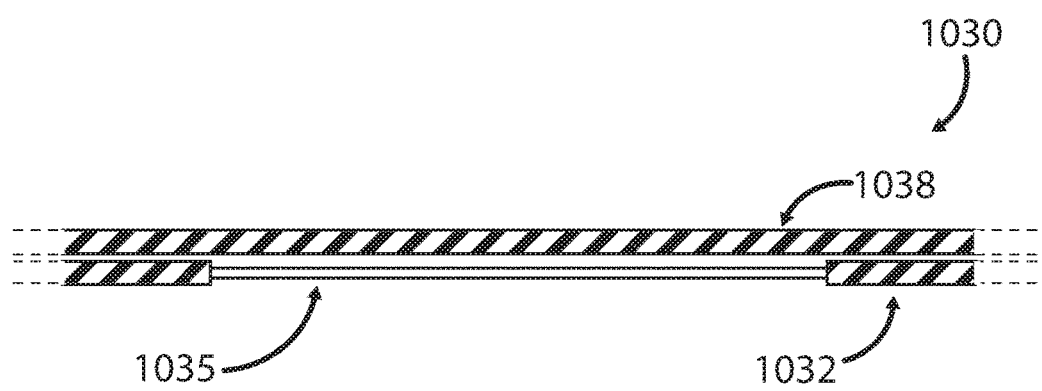

FIGS. 10A-10C show partial cross-sectional views of attachment apparatus straps 1030 which are configured to accommodate body movements associated with breathing. The strap 1030 includes a stretchable section 1035 positioned between two substantially non-stretchable portions 1032 of the strap. The strap 1030 further includes an additional substantially non-stretchable layer 1038 located on top of (or underneath) the stretchable section 1035 and attached at its ends to the strap's non-stretchable portions 1032, such that the stretchable section 1035 cannot stretch beyond the length of layer 1038, or more specifically, beyond the length of that portion of layer 1038 which is positioned above the stretchable section 1035 and between the two non-stretchable portions 1032. FIG. 10A shows the strap 1030 when the stretchable section 1035 is at its most relaxed state, i.e., at the end of exhalation. When the stretchable section 1035 is in its relaxed state, the substantially non-stretchable layer 1038 folds and forms an "omega"-like (Ω) shape. FIG. 10B shows the strap 1030 when the stretchable section 1035 is partially stretched and the non-stretchable layer 1038 is partially straightened correspondingly. FIG. 10C shows the stretchable section 1035 maximally stretched, such that it reaches the length of the top layer 1038, i.e., at the end of inhalation. When the stretchable section 1035 is maximally stretched, the non-stretchable layer 1038 and the stretchable section 1035 may be substantially parallel. Thus, the shape of layer 1038 may indicate to the user if the attachment apparatus is properly attached to the patient's body, i.e., if the attachment enables both stretching and relaxing of the stretchable section 1035, which is required in order to accommodate the movements of the patient's body during the breathing cycle. If the strap is at the state shown in FIG. 10A upon attachment, and the patient is not at the end of exhalation, this indicates to the user that the strap 1030 is too loose and should be tightened. If the strap is at the state shown in FIG. 10C upon attachment, and the patient is not at the end of inhalation, this indicates to the user that the strap 1030 is too tight and should be loosened.

FIG. 11A shows an attachment apparatus having straps which are configured to accommodate body movements associated with breathing. The attachment apparatus 1100 may include a mounting base 1120 for receiving the medical device thereon. The mounting base 1120 may be connected to a back base (not shown in FIG. 11A) of the attachment apparatus 1100, and/or secured to the patient's body directly, using a plurality of straps 1130. The straps 1130 may be connected to the mounting base 1120 via dedicated connectors 1140. In some implementations, the straps 1130 may include one or more stretchable sections (not shown), which may be provided inside the strap connector 1140. The strap connector 1140 may include an indicator 1150 to indicate to the user if the attachment is proper, i.e., if it enables the stretching and relaxing of the stretchable section/s of the strap as required in order to accommodate the movements of the patient's body during the breathing cycle. The indicator 1150 may be configured as an indication bar provided with a dial 1152, which is associated with the stretchable section/s of the strap 1130, such that the dial 1152 moves along the indication bar as the stretchable section stretches and relaxes. The indication bar may further include at least one marking 1154 to assist the user in establishing a proper connection of the straps 1130. For example, the marking 1154 may be an "OK" marking located at the center of the indication bar 1150, as shown in FIG. 11A, such that proper attachment of the straps 1130 is achieved when the dial 1152 is positioned substantially at the location of the "OK" marking. FIG. 11B depicts the indicator 1150 during the end of inhalation. During inhalation, the stretchable section of the strap 1130 stretches such that the dial 1152 moves toward the distal end of the indication bar, the distal end being the end farthest from the mounting base 1120. When the end of inhalation is reached, the dial 1152 may be located at the distal end of the indication bar, which indicates that the stretchable section of the strap is maximally stretched. FIG. 11C depicts the indicator 1150 during the end of exhalation. During exhalation, the stretchable section returns to its relaxed state, resulting in the dial 1152 moving toward the proximal end of the indication bar, the proximal end being the end closest to the mounting base 1120. In some implementations, when end of exhalation is reached, the dial 1152 may be located at the proximal end of the indication bar, which may indicate that the stretchable section of the strap is at its most relaxed state.

FIGS. 12A-12C show three steps of attaching a medical device to the patient's body using an exemplary attachment apparatus having a mounting base.

FIG. 12A shows the patient lying on the back base 1210 of the attachment apparatus 1200, after the back base 1210 has been placed on the patient bed 125, and prior to placement of the mounting base 1220 on the patient's body. In some implementations, the attachment apparatus 1200 may include one or more straps 1230a fixedly attached to the mounting base 1220, and one or more straps 1230b which are fixedly attached to the back base 1210 and can be attached to the mounting base 1220. The straps 1230b may have at their free ends, i.e., the ends not attached to the back base 1210, a portion of a coupling mechanism 1232, such as a female portion of a snap buckle, as shown in FIG. 12A, which can mate with another portion of the coupling mechanism 1224, such as a male portion of a buckle, which may be provided either on the mounting base 1220, as shown in FIG. 12A, or at the free ends of additional straps (not shown) which are attached to the mounting base 1220.

FIG. 12B shows the attachment apparatus 1200 after the mounting base 1220 has been placed on the patient's body and secured thereto via connection of the straps' female portion of a buckle 1232 to the mounting base's male portion of the buckle 1224. It can be appreciated that the coupling mechanism between the straps 1230b and the mounting base 1220 is not limited to buckles, and it may otherwise be in the form of snaps, hooks and loops fasteners, or any other suitable coupling mechanism.

FIG. 12C shows the medical device 128 coupled to the mounting base 1220 and ready for operation. In some implementations, the interface between the medical device 128 and the mounting base 1220 may be such that the medical device 128 can be rotated, either via rotation of the mounting base 1220 or via rotation of the medical device 128 on top of the mounting base 1220, to allow the user to choose the optimal positioning of the medical device 128. Optimal positioning may be based on the characteristics of the patient's body and/or the location of the target of the procedure, the optimal insertion angle of the medical tool, etc.

Figure 13A:
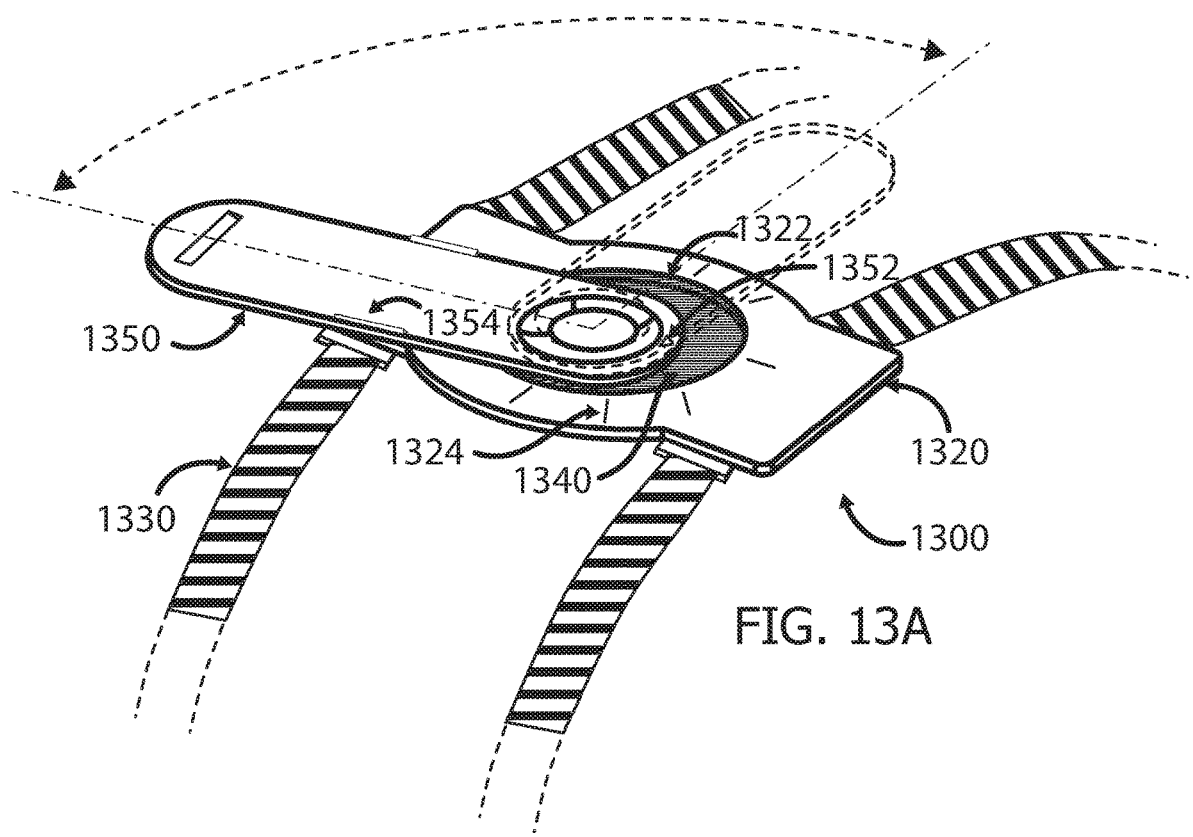
FIGS. 13A-13B show an exemplary mounting base which enables position adjustment and/or rotation of a medical device coupled thereto.

FIG. 13A shows a mounting base 1300 which enables position adjustment and/or rotation of a medical device coupled thereto. The mounting base 1300 may be connected to a back base (not shown in FIG. 13A) of the attachment apparatus, or secured to the patient's body directly, using a plurality of straps 1330.

In some implementations, the mounting base 1300 may include a stationary plate (or base) 1320, to which the straps 1330 are connected, either fixedly or removably, and a moveable plate 1340, which is coupled to the stationary plate 1320. The coupling between the stationary plate 1320 and the moveable plate 1340 may be such that the moveable plate 1340 can be moved relative to the stationary plate 1320. In some implementations, the moveable plate 1340 may be annular and positioned within an annular portion 1322 of the stationary plate 1320. In such implementations, the diameter of the outer rim of the moveable plate 1340 should be smaller than the diameter of the outer rim of the annular portion 1322 of the stationary plate 1320, but larger than the diameter of the inner rim of the annular portion 1322 of the stationary plate 1320, so as to ensure that at all times at least a portion of the moveable plate 1340, preferably along its entire circumference, is securely positioned between two layers (not shown) of the stationary plate, or underneath the stationary plate 1320, or in any other manner which allows movement of the moveable plate 1340 relative to the stationary plate 1320, with no risk of the moveable plate 1340 separating or disconnecting from the stationary plate 1320. Such coupling enables movement of the moveable plate 1340 in all directions, the maximal distance of movement being equal to the maximal difference between the diameters of the outer rim of the moveable plate 1340 and the outer rim of the annular portion 1322 of the stationary plate 1320.

Thus, if after coupling the medical device to the mounting base 1300, the physician realizes that the positioning of the medical device is not accurate, such that the medical tool cannot be aligned with the chosen entry point at the desired entry angle, for example, then instead of decoupling the device from the mounting base 1300, removing and reattaching the mounting base 1300 to the patient's body and then recoupling the device to the mounting base 1300, the position of the medical device can be more easily adjusted by moving the moveable plate 1340 as needed. In some implementations, the movement of the moveable plate 1340 may be executed manually by the user (e.g., physician). In other implementations, the moveable plate 1340 may be connected to a controller (not shown), such that the movement may be executed automatically and/or remotely controlled. The described mechanism enables the minimization of the movement mechanism of the medical device, and thus a minimization of the overall size of the medical device, since in this case the movement mechanism of the device does not need to execute large movements of the device and can be used for fine tuning only.

The mounting base 1300 may further include a rotating plate 1350 coupled to the moveable plate 1340, in order to enable also rotation of the medical device about an axis following its coupling to the mounting base 1300. Rotation of the medical device may be needed, for example, for orientating an insertion device according to the optimal needle insertion angle or for preventing imaging artifacts by distancing the device from the area about to be scanned. The rotation range may be 360 degrees or it may be otherwise restricted. In some implementations, the rotation may be executed manually by the user. In other implementations, the rotating plate 1350 may be connected to a controller (not shown), such that the rotation may be executed automatically and/or remotely controlled.

In some implementations, the annular portion 1322 of the stationary plate 1320 may include a plurality of markings (or—scales) 1324 along at least a portion of its circumference, and the rotating plate 1350 may include an indicator, such as an arrowhead 1352, to guide the rotation of the rotating plate 1350 to its required position. For example, it can be determined that the rotating plate 1350 should be rotated until the arrowhead 1354 points to a specific marking on the stationary plate 1320.

In some implementations, the rotating plate 1350 may include a coupling mechanism to receive the medical device and secure it thereto, such as latches 1354 which mate with corresponding notches (not shown) in the medical device, a magnetic coupling mechanism, etc. The rotating plate 1350 shown in FIG. 13A includes three latches 1354, one latch at the distal end of the rotating plate 1350 ("distal end" being the end farthest from the moveable plate 1340) and two latches positioned substantially opposite each other along the length of the rotating plate 1350. In alternative implementations, the rotating plate 1350 may be part of the medical device, either an integral part of the medical device, or more specifically of the base of the medical device, or a removably attachable part. In such cases, the rotating plate 1350 and/or the moveable plate 1340 of the mounting base 1300 may include a coupling mechanism (not shown) for removably coupling the rotating plate 1350 of the medical device to the moveable plate 1340 of the mounting base 1300.

In addition, the mounting base 1300 may include at least one lock (not shown), such as a ratchet mechanism or a dedicated fastener, to maintain the desired position of the medical device after the moveable plate 1340 has been moved and/or the rotating plate 1350 has been rotated as needed to achieve the desired position of the medical device.

Figure 13B:
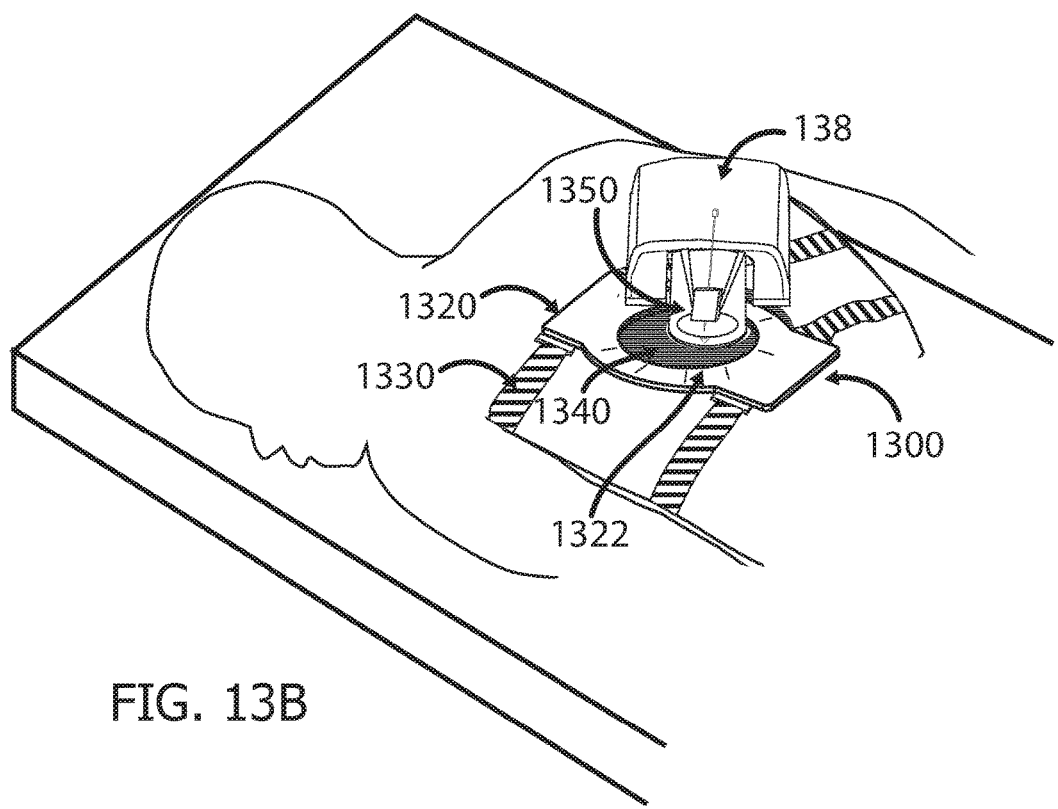

FIG. 13B shows the mounting base 1300 attached to the patient using the straps 1330 and the medical device 138 coupled to the mounting base 1300. It can be seen that in comparison to the positions of the moveable plate 1340 and the rotating plate 1350 in FIG. 13A, in FIG. 13B the moveable plate 1340, and thus also the attached rotating plate 1350, has been moved relative to the annular portion 1322 of the stationary plate 1320, and the rotating plate 1350 has also been rotated approximately 60-70 degrees clockwise.

FIGS. 14A and 14B show another implementation of an attachment apparatus 1400, which comprises a mounting base 1420 and a plurality of weights 1440 connected to the mounting base 1420 via straps 1430.

FIG. 14A shows the mounting base 1420 positioned on the patient's chest/abdomen, such that one pair of weights falls to the right side of the patient's body and the second pair of weights falls to the left side of the patient's body (only the right pair of weights is shown in FIG. 14A). The weights 1440 are pulled downwards by gravity, and since the two pairs of weights are pulled downwards on two opposite sides of the patient's body, the weight of the weights 1440 holds down the mounting base 1420 and maintains its position on the patient's body. If the medical device is intended to insert a needle, or any other insertable medical tool, into the patient's body, the weight of the weights should be calculated such that they support the required perpendicular insertion force. It can be appreciated that the number of weights used may vary and the weight of each weight may vary accordingly.

In some cases, depending on the weights' size and/or their material, the weights may cause imaging artifacts which may impair the analysis of the scan. Thus, the attachment apparatus 1400 may be configured such that it allows adjustment of the weights' positioning, keeping the space S intended for scanning devoid of weights. For example, the weights 1440 may be coupled to a bar 1450 along which the weights 1440 can be moved, such as via a rail (not shown). It can be appreciated that the weights 1440 may alternatively be connected directly to the medical device, e.g., by means of the hooks and anchors shown in FIGS. 15A-15D hereinbelow, whether a mounting base is or is not utilized.

FIG. 14B shows another weight-based attachment apparatus 1410, in which the weights (only two weights 1440a, 1440b are shown in FIG. 14B) are connected to the mounting base 1420 such that they can pivot about an axis. The pivoting may be enabled by using rotatable connectors, such as the connectors shown in FIG. 9A), or it may be a result of the connection between the straps 1430 and the mounting base 1420, either directly or via connectors, e.g., connectors may be fixed at a certain degree relative to the mounting base 1420, and the straps 1430 may slide along the circumference of the connectors. The ability to rotate the straps 1430 allows a much-desired flexibility in the location and orientation of the attachment apparatus 1400, and thus the medical device, on the patient's body. For example, if the procedure to be performed requires positioning the medical device on the patient's upper chest or back, some of the weights may hang to the side of the patient's body, in this case weight 1440a and the corresponding weight on the opposite side of the patient's body (not shown), and some of the weights can hang over the patient's shoulder, in this case weight 1440b and the corresponding weight on the opposite side of the patient's body (not shown), providing the mounting base 1420, and thus the medical device, with enhanced stability and durability.

It can be appreciated that the weights 1440a and 1440b may alternatively be connected directly to the medical device, e.g., by means of the hooks and anchors shown in FIGS. 15A-15D hereinbelow, whether a mounting base is or is not utilized.

In some implementations, the entire medical device may be a single-use disposable device which undergoes sterilization at the end of the manufacturing process. In other implementations, the medical device may be at least partially reusable and/or comprised of components which cannot undergo sterilization. For example, if the medical device is an insertion device, the insertable medical tool (e.g., needle) may be disposable and as such provided sterile and discarded after a single use, whereas the rest of the device may be reusable and provided non-sterile. If a non-sterile device comes in contact with the patient's body, the patient may be infected with a variety of bacteria and other contaminants, which may be hazardous to his/her health. Further, during the medical procedure, the patient's blood and other bodily fluids and tissues may soil the device, and since the device is reusable, there's a risk of cross-contamination between patients. Thus, prior to commencing the medical procedure, the medical device must be sufficiently draped such that no non-sterile component of the device will contact the patient and/or any person or instrument which comes in contact with the patient during the medical procedure, and that no non-sterile component of the device will be exposed to blood splatters, etc. Accordingly, an attachment apparatus intended to receive a medical device which requires draping, must be coupled to the medical device such that the sterile environment is not compromised.

Figure 15A:
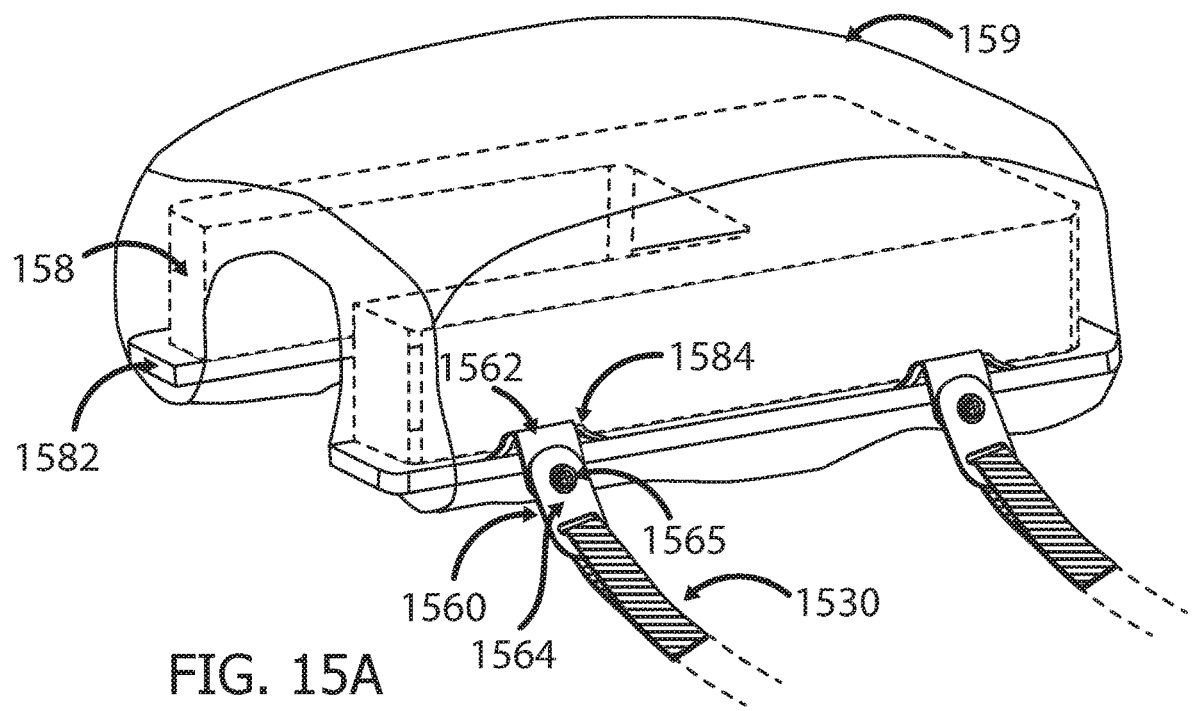
FIGS. 15A-15D show exemplary attachment apparatus adapted to be coupled to a medical device covered by a drape while maintaining a sterile environment.

FIG. 15A shows a medical device 158 covered by a drape 159 and having straps 1530 of an attachment apparatus coupled thereto. The base 1582 of the medical device 158 may comprise anchors 1584 for securing the straps 1530 to the medical device 158. The anchors 1584 may be positioned such that the connection takes place higher than skin level, in order to produce larger perpendicular forces and thus to provide a more durable and stable attachment of the medical device to the body. In some implementations, the anchors 1584 may be connected to the housing of the device 158. The straps 1530 may be provided with strap connectors 1560 which include a hook member 1562 that engages with the anchor 1584 of the medical device 158, over the drape 159, such that the sterile environment is not compromised. In some implementations, the hook member 1562 may be coated, at least partially, with a resilient material, such as rubber, sponge, etc., and/or it may have rounded corners, for example, to prevent the hook 1562 from ripping through the drape sheet 159. Further, the section of the drape sheet 159 over which the hook member 1562 latches on to the anchor 1584 may be reinforced, for example, it may have a double layer or a sticker attached thereon.

In some implementations, the strap connector 1560 may further include a rotating member 1564 coupled to the hook member 1562, such as via a hinge 1565, to allow adjustment of the strap's location via pivoting of the strap 1530 after the hook 1562 has been coupled to the anchor 1584. In such implementations, the strap 1530 is attached to the rotating member 1564 of the connector 1560.

Figure 15B:
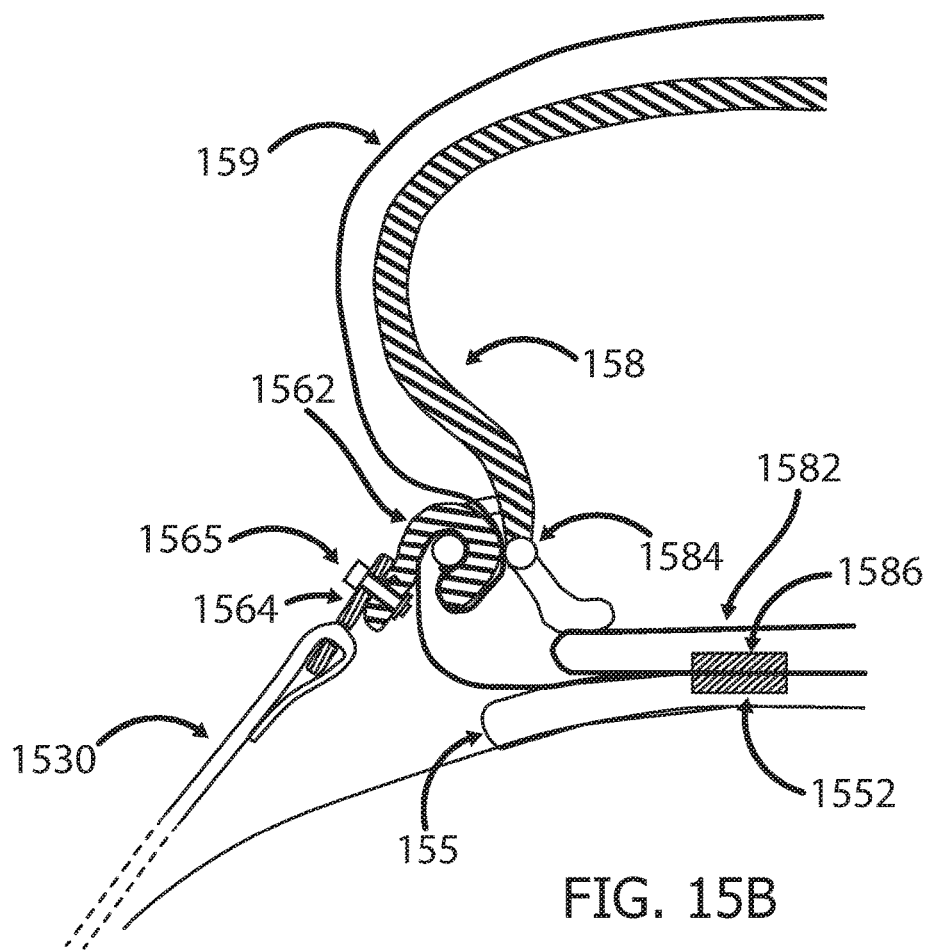

FIG. 15B shows a cross-sectional view of the coupling between a draped medical device 158 and an attachment apparatus. As shown, the hook member 1562 is engaged with the anchor 1584 on the device's base 1582 over the drape 159, such that the sterile environment remains intact. The hook member 1562 is coupled to the rotating member 1564 via a hinge 1565, and the strap 1530 is coupled to the rotating member 1564. FIG. 15B further shows an intermediary element 155, which may be a pad/cushion or a mounting base, as described in detail above. In some implementations, the medical device 158 may be coupled to the intermediary element 155, with the drape 159 positioned therebetween. Such coupling may be established, for example, using a mechanical mechanism, or a magnetic mechanism, e.g., the intermediary element 155 may include magnetic material 1552 and the medical device's base 1582 may include a metal portion 1586, or vice versa. The intermediary element 155 may be merely placed on the patient's body, such that the straps 1530 alone attach the medical device 158 to the patient's body, or it may be adhered to the patient's body using a low adherence glue, for example, such that the straps 1530 are complementary to the adhesive to ensure a durable attachment.

Figure 15C:
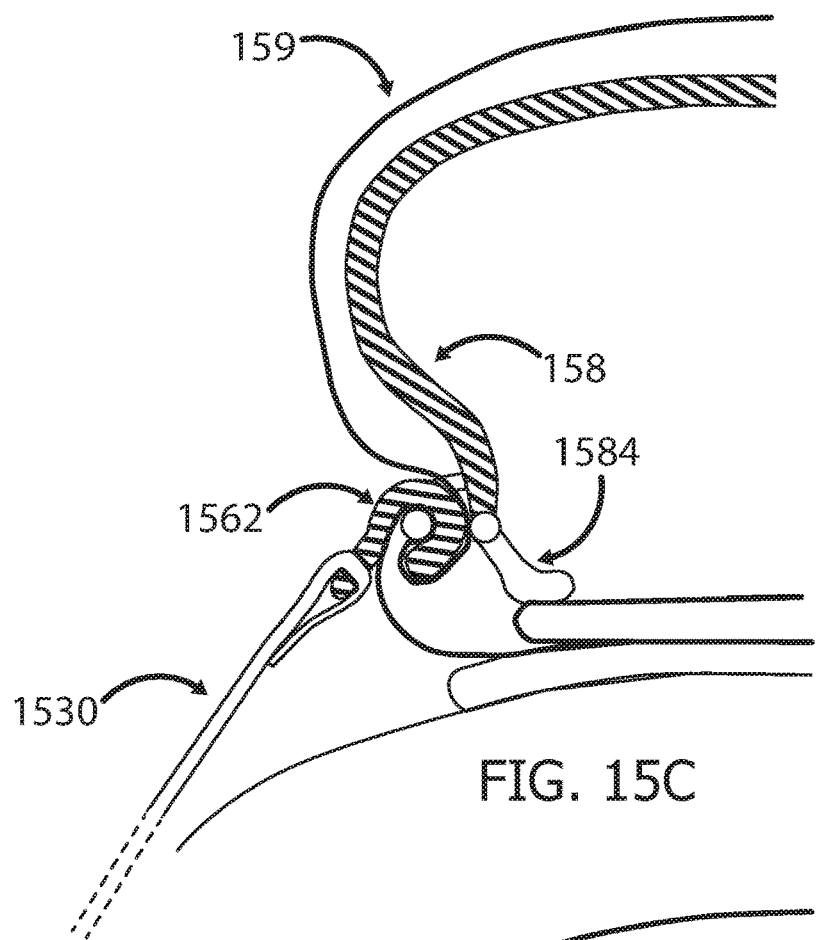

FIG. 15C shows a cross-sectional view of the coupling between a draped medical device 158 and another attachment apparatus implementation, in which no rotating member 1564 is employed. In such implementations, the straps 1530 may be connected directly to the hook member 1562.

In some implementations, the hook member 1562 may be passed through an opening (not shown) in the drape 159, such that the strap 1530 is connected to the hook member 1562, either directly, similarly to the connection shown in FIG. 15C, or via a rotating member 1564, similarly to the connection shown in FIG. 15B. In order to maintain a sterile environment, the drape may be re-sealed via welding or adhering it around the passing-through hook member 1562.

Figure 15D:
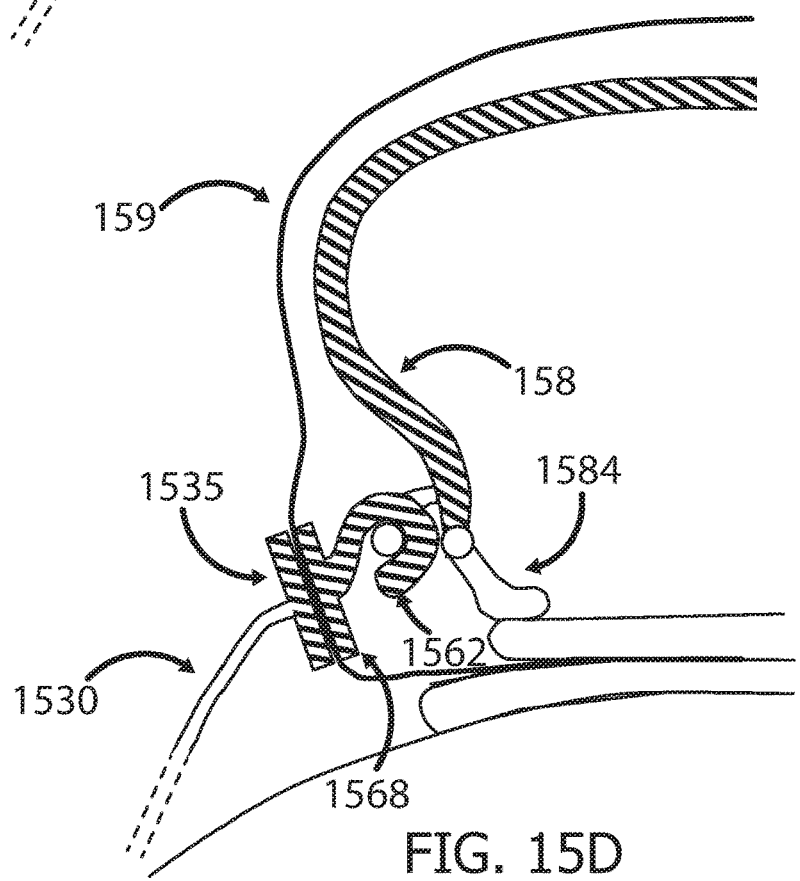

FIG. 15D shows a cross-sectional view of the coupling between a draped medical device 158 and yet another the attachment apparatus implementation, in which the hook members 1562 are attached to the inner (non-sterile) side of the drape 159, and the straps 1530 are attached to the outer (sterile) side of the drape 159. Such implementations minimize the risk of the drape 159 being breached by the hook member 1562. The attachment of the hooks 1562 and the straps 1530 to the drape 159 may be carried out using an adhesive, ultrasonic welding, etc., and the attachment position may be such that the straps 1530 and the hook members 1562 are positioned at the same location, on opposite sides of the drape 159. In some implementations, the hook member 1562 and the strap 1530 may be provided with dedicated bases 1568, 1535 respectively, for attachment to the drape 159.

Although particular implementations have been disclosed herein in detail, this has been done by way of example for purposes of illustration only, and is not intended to be limiting with respect to the scope of the appended claims, which follow. In particular, it is contemplated that various substitutions, alterations, and modifications may be made without departing from the spirit and scope of the disclosure as defined by the claims. Other aspects, advantages, and modifications are considered to be within the scope of the following claims. The claims presented are representative of the implementations and features disclosed herein. Other unclaimed implementations and features are also contemplated. Accordingly, other implementations are within the scope of the following claims.

The invention claimed is:

1. An apparatus for attaching a medical device to a body of a subject, the apparatus comprising:
   a back base configured to be positioned between the body of the subject and a surface adapted for the subject to lie thereon;
   at least one set of straps configured to be connected to said back base and to at least one of said medical device and an intermediary element configured for securing to the body of the subject and for receiving said medical device thereon; and
   at least one set of connectors configured to provide a connection between said at least one set of straps and one or more of said medical device, said intermediary element and said back base;
   wherein one or more connectors of said at least one set of connectors is configured to enable pivoting of at least a portion of said one or more connectors about an axis; and
   wherein said apparatus is configured to prevent substantially any relative movement between said medical device and the body of the subject upon attachment of said medical device to the body of the subject either directly or using said intermediary element.

2. The apparatus of claim 1, wherein said at least one set of connectors comprises a first set of connectors configured to provide a connection between said at least one set of straps and said back base and a second set of connectors configured to provide a connection between said at least one set of straps and said at least one of said medical device and said intermediary element.

3. The apparatus of claim 1, wherein said one or more connectors comprise at least two coupled portions, wherein a first of said at least two coupled portions is configured to be attached to said at least one of said medical device and said intermediary element and a second of said at least two coupled portions is configured to be attached to a strap of said at least one set of straps.

4. The apparatus of claim 1, wherein one or more straps of said at least one set of straps comprise at least one stretchable section configured to stretch along a longitudinal axis of said one or more straps.

5. The apparatus of claim 4, further comprising an indicator configured to indicate the extent of said stretching of said at least one stretchable section.

6. The apparatus of claim 1, wherein one or more connectors of said at least one set of connectors comprise a hook configured to be coupled to an anchor of said at least one of said medical device and said intermediary element.

7. The apparatus of claim 6, wherein said hook and one or more straps of said at least one set of straps are configured to be attached to a drape covering said medical device, on either side of said drape.

8. The apparatus of claim 1, further comprising a respiration sensor configured to sense a characteristic associated with the breathing of the subject.

9. The apparatus of claim 1, wherein said back base is configured to enable adjustment of at least one of the length and the width of said back base.

10. The apparatus of claim 1, wherein said intermediary element comprises a mounting base, said mounting base including one or more coupling members configured to couple said medical device thereto.

11. The apparatus of claim 10, wherein said mounting base is configured to enable movement of said medical device relative to at least a portion of said mounting base upon coupling said medical device to said mounting base.

12. The apparatus of claim 11, wherein said mounting base comprises a stationary plate and a moveable plate configured to be connected to said stationary plate, said moveable plate being moveable relative to said stationary plate.

13. The apparatus of claim 12, wherein said mounting base further comprises a rotatable plate configured to be connected to said moveable plate and configured to pivot about an axis of connection to said moveable plate.

14. The apparatus of claim 1, wherein said intermediary element comprises at least one flexible pad.

15. The apparatus of claim 14, wherein said at least one flexible pad comprises a granular material enclosed within a flexible covering, and wherein said at least one flexible pad is configured to transform from a moldable state to a more structurally stable state by means of application of vacuum to said at least one flexible pad.

16. The apparatus of claim 14, wherein said at least one flexible pad includes one or more markers positioned either on or inside said at least one flexible pad, said markers being detectable by an imaging system.

17. The apparatus of claim 1, wherein said surface is a bed of an imaging system.

18. The apparatus of claim 1, wherein said at least one set of straps comprises a first set of straps configured to be connected to said back base, and a second set of straps configured to be connected to said at least one of said medical device and said intermediary element.

19. The apparatus of claim 18, wherein one or more straps of said first set of straps is configured to be connected to one or more straps of said second set of straps.

20. The apparatus of claim 1, wherein said back base comprises at least two portions moveable relative to each other.

* * * * *

UNITED STATES PATENT AND TRADEMARK OFFICE
CERTIFICATE OF CORRECTION

PATENT NO. : 11,103,277 B2  
APPLICATION NO. : 16/092786  
DATED : August 31, 2021  
INVENTOR(S) : Arnold et al.

Page 1 of 1

It is certified that error appears in the above-identified patent and that said Letters Patent is hereby corrected as shown below:

In the Specification

Column 4, Lines 29-46 should read:
In some implementations, the mounting base may include a plurality of bases/plates which enable position adjustment and/or rotation of the medical device coupled thereto. Rotation of the medical device may be needed, for example, for orientating an insertion device according to an optimal needle insertion angle or for preventing imaging artifacts. In some implementations, the mounting base may include a stationary plate, a moveable plate coupled to the stationary plate and a rotating plate coupled to the moveable plate. The moveable plate may enable restricted movement in all directions and the rotating plate may enable pivoting about an axis. Once the desired positioning is achieved, the user ensures that the positioning is maintained by locking the plates of the mounting base such that they can no longer move/rotate. The rotating plate may alternatively be part of the medical device base such that the user couples the rotating plate to the moveable plate upon coupling of the medical device to the mounting base.

Column 18, Lines 44-51 should read:
To eliminate the above risks, the straps which attach the medical device to the patient's body may include one or more elastic (or--flexible) sections, which can stretch during inhalation and return to their relaxed state during exhalation, thus ensuring that the straps do not become too tight during inhalation so as to cause the patient discomfort, and do not become too loose during exhalation so as to enable undesired movement of the medical device relative to the patient's body.

Column 24, Lines 42-44 should read:
FIG. 15D shows a cross-sectional view of the coupling between a draped medical device 158 and yet another attachment apparatus implementation, in which the hook Signed and Sealed this  
Seventh Day of December, 2021

Drew Hirshfeld  
*Performing the Functions and Duties of the*  
*Under Secretary of Commerce for Intellectual Property and*  
*Director of the United States Patent and Trademark Office*